(12) United States Patent
Forrester et al.

(10) Patent No.: US 8,759,775 B2
(45) Date of Patent: Jun. 24, 2014

(54) METHOD OF DETECTING CONTAMINANTS

(75) Inventors: Sean Thomas Forrester, Richmond (AU); Michael John McLaughlin, Fullarton (AU); Leslie Joseph Janik, McLaren Flat (AU)

(73) Assignee: Commonwealth Scientific and Industrial Research Organisation, Campbell, Australian Capital Territory (AU)

( * ) Notice: Subject to any disclaimer, the term of this patent is extended or adjusted under 35 U.S.C. 154(b) by 38 days.

(21) Appl. No.: 13/380,241

(22) PCT Filed: Jun. 25, 2010

(86) PCT No.: PCT/AU2010/000804
§ 371 (c)(1), (2), (4) Date: Feb. 27, 2012

(87) PCT Pub. No.: WO2010/148458
PCT Pub. Date: Dec. 29, 2010

(65) Prior Publication Data
US 2012/0153160 A1    Jun. 21, 2012

(30) Foreign Application Priority Data

Jun. 25, 2009 (AU) .............................. 2009902946
Feb. 23, 2010 (AU) .............................. 2010900753

(51) Int. Cl.
*G01N 21/35*       (2006.01)
(52) U.S. Cl.
USPC ................................................... 250/339.12
(58) Field of Classification Search
USPC ....................................... 250/339.01–339.15
See application file for complete search history.

(56) References Cited

U.S. PATENT DOCUMENTS

| 4,661,706 | A  | * | 4/1987  | Messerschmidt et al. . 250/341.8 |
| 4,771,176 | A  | * | 9/1988  | Schiefer et al. .......... 250/339.13 |
| 6,087,662 | A  | * | 7/2000  | Wilt et al. ................ 250/339.12 |
| 6,697,654 | B2 | * | 2/2004  | Lorenz et al. ................. 600/310 |
| 8,330,109 | B2 | * | 12/2012 | Werner et al. ............ 250/339.09 |
| 2010/0015714 | A1 | * | 1/2010 | Saini et al. ...................... 436/25 |

FOREIGN PATENT DOCUMENTS

WO    WO 2009/074815       *  6/2009   ............. E21B 21/06
WO    WO 2009/074815 A2       6/2009

OTHER PUBLICATIONS

Percherancier et al. "Fourier Transform Infrared Spectrometry to Detect Additives and Contaminants in Insulating Oils" Electrical Insulation Magazine, IEEE, vol. 14, No. 3, pp. 23-29, 1998.*
Malley, D.F., et al., "Analysis of diesel Fuel Contamination in Soils by Near-Infrared Reflectance Spectrometry and Solid Phase Microextraction-Gas chromatography"; *Journal of Soil Contamination*, vol. 8, No. 4, pp. 481-489 (1999).
Geladi, P., et al; "Partial Least-Squares Regression: A Tutorial"; *Analytica Chimica Acta*, vol. 185, pp. 1-17 (1986).

(Continued)

*Primary Examiner* — David Porta
*Assistant Examiner* — Edwin Gunberg
(74) *Attorney, Agent, or Firm* — Nixon & Vanderhye, P.C.

(57) ABSTRACT

Method for the selective detection of petroleum hydrocarbon in an environmental sample containing natural organic matter. The method includes subjecting the sample to infrared (IR) radiation, and detecting an IR signal centered on a signal at 1380 cm$^{-1}$, 2690 cm$^{-1}$, 2730 cm$^{-1}$, 2830 cm$^{-1}$, 2870 cm$^{-1}$, 4164 cm$^{-1}$, 4256 cm$^{-1}$, 4329 cm$^{-1}$ and/or 4388 cm$^{-1}$. Detection of the IR signal indicates the presence of petroleum hydrocarbon in said sample.

12 Claims, 13 Drawing Sheets

(56) References Cited

OTHER PUBLICATIONS

Gomez, R.S.G., et al; "Spectroscopic Determination of Poly-Aromatic Compounds in Petroleum Contaminated Soils"; *Water, Air, and Soil Pollution*, vol. 158, pp. 137-151 (2004).

Janik, L.J., et al; "Can mid infrared diffuse reflectance analysis replace soil extractions?"; *Australian Journal of Experimental Agriculture*, vol. 38, pp. 681-696 (1998).

Nadim, F., et al; A Comparison of Spectrophotometric and Gas Chromatographic Measurements of Heavy Petroleum Products in Soil Samples; *Water, Air, and Soil Pollution*, vol. 134, pp. 97-109 (2002).

Reeves, III, J.B., et al; "Near infrared reflectance spectroscopy for the analysis of agricultural soils"; *J Near Infrared Spectrosc.*, vol. 7, pp. 179-193 (1999).

McCarty, G.W., et al; "Mid-Infrared and Near-Infrared Diffuse Reflectance Spectroscopy for Soil Carbon Measurement"; *Soil Science Society of America Journal*, vol. 66, No. 2, pp. 640-646 (2002).

Sadler, R., et al; "Analytical Methods for the Determination of Total Petroleum Hydrocarbons in Soil"; *Proceedings of the Fifth National Workshop on the Assessment of Site Contamination*; pp. 133-150 (2003).

Zwanziger, H.W., et al; "Near infarred spectroscopy of fuel contaminated sand and soil. I. preliminary results and calibration study"; *J. Near Infrared Spectrosc.*, vol. 6, pp. 189-197 (1998).

Adams, M.J., et al; "Prediction of oil yield from oil shale minerals using diffuse reflectance infrared Fourier transform spectroscopy"; *Fuel*, vol. 84, pp. 1986-1991 (2005).

Ewing, K.J., et al; "Fiber optic infrared reflectance probe for detection of hydrocarbon fuels in soil"; *SPIE*, vol. 2367, pp. 17-23 (1995).

Schneider, I., et al; "Fiber-Optic Near-Infrared Reflectance Sensor for Detection of Organics in Soils"; *IEEE Photonics Technology Letters*, vol. 7, No. 1, pp. 87-89 (1995).

International Search Report for PCT/AU2010/000804, mailed Aug. 3, 2010.

Written Opinion of the International Searching Authority for PCT/AU2010/000804, mailed Aug. 3, 2010.

International Preliminary Report on Patentability for PCT/AU2010/000804, dated Apr. 11, 2011.

Written Opinion of the International Preliminary Examining Authority, mailed May 23, 2011.

Himmelsbach, D.S., et al; "Development and use of an Attenuated total Reflectance/Fourier Transform Infrared (ATR/FT-IR) Spectral Database to Identify Foreign Matter in Cotton"; *Journal of Agricultural and Food Chemistry*; vol. 54, pp. 7405-7412 (2006).

Grabiec-Raczak, et al; "Determination of oil in environmental samples using FTIR spectrometry technique"; Proceedings ECOpole'05, Ksiega Konferencyjna/Proceedings, 14th, Oct. 20-22, 2005, 2006:897967 CAPLUS (Abstract).

Hazel, G., et al; "Multivariate Analysis of Mid-IR FT-IR Spectra of Hydrocarbon-Contaminated Wet Soils"; *Applied Spectroscopy*, vol. 51, No. 7, pp. 984-989 (1997).

Pejcic, B., et al; "Mid-Infrared Sensing of Organic Pollutants in Aqueous Environments"; *Sensors*, vol. 9, pp. 6232-6253 (2009).

Janik, L.J., et al; "The prediction of soil chemical and physical properties from mid-infrared spectroscopy and combined partial least-squares regression and neural networks (PLS-NN) analysis"; *Chemometrics and Intelligent Laboratory Systems*, vol. 97, pp. 179-188 (2009).

Minty, B., et al; "Analysis of oil in water at the low ppm level using direct supercritical fluid extraction coupled on-line with infrared spectroscopy"; *Anal. Commun.*, vol. 35, pp. 277-280 (1998).

Svarovskaya, L.I., et al; "Biodegradation of Petroleum Hydrocarbons by Soil Microflora Activated with Photoluminescent Films"; *Petroleum Chemistry*, vol. 47, No. 3, pp. 219-224 (2007).

Matejka, Pavel, "NIR Spectrometry"; available at www.vscht.cz/anl/vibspec/NIR%20spectrometry.pdf (1999).

Castro, A.T.; "NMR and FTIR Characterization of Petroleum Residues: Structural Parameters and Correlations"; *J. Braz. Chem. Soc.*, vol. 17, No. 6, pp. 1181-1185 (2006).

White, D.M., et al; "The bituminous material in Arctic peat: implications for analyses of petroleum contamination"; *Journal of Hazardous Materials*; vol. 49, pp. 181-196 (1996).

\* cited by examiner

METHOD OF DETECTING CONTAMINANTS

The present invention relates to the identification of an infrared (IR) signal in the range of 1360 cm$^{-1}$ to 2090 cm$^{-1}$ and/or 2650 cm$^{-1}$ to 3000 cm$^{-1}$, and/or 3700 cm$^{-1}$ to 4400 cm$^{-1}$ that can be used as an indicator of the presence of petroleum hydrocarbon. In a particular application, the invention provides a method for the detection of petroleum hydrocarbon in an environmental sample such as a soil, silt, sediment, rock, mineral or waste sample.

PRIORITY

This application is the U.S. national phase of International Application No. PCT/AU2010/000804 filed on 25 Jun. 2010, which designated the U.S. and claims priority from Australian Provisional Patent Application 2009902946, titled "METHOD OF DETECTING CONTAMINANTS", and filed on 25 Jun. 2009; and Australian Provisional Patent Application 2010900753, titled "METHOD OF DETECTING CONTAMINANTS", and filed on 23 Feb. 2010.

The entire content of these applications are hereby incorporated by reference.

BACKGROUND

Most petroleum hydrocarbon substances are derived from crude oil and, typically, comprise a mixture of short and medium length hydrocarbon compounds. The less volatile components of petroleum hydrocarbons can become environmental contaminants; they may remain in the environment for extended periods and become toxic to wildlife, flora and/or humans. Such contaminations are usually difficult, if not impossible, to observe visually unless gross contamination has occurred. Therefore, methods for the rapid and/or simple detection of petroleum hydrocarbons in the environment (ie as may be found in soils, sludges and waterways) are desirable for monitoring environmental contamination and/or assessing a site. For example, methods for the rapid detection of petroleum hydrocarbons are particularly useful in assessing or monitoring contamination of coastal land following off-shore oil spills.

For instance, with high urban growth, city fringes are gradually encroaching on areas that were formerly disused and/or predominantly industrial in nature. These sites present usable and valuable property for the further growth and development of many industrialised cities. However, many such sites have been contaminated by petroleum hydrocarbon leakage from their previous industrial uses, and some have been exposed to these recalcitrant materials time and time again. While these sites hold great potential, the environmental protection guidelines of most industrialised countries set safety standards for the minimum acceptable concentration of petroleum hydrocarbons in soils or other environmental matrices. Thus, to be placed in order for non-industrial reuse (eg residential or light-industrial uses), the amount of petroleum hydrocarbon on these sites must be reduced to acceptable levels for their intended future use. While many options are available for the treatment of contaminated sites, a significant portion of the time and costs involved in treating these sites is consumed in the monitoring of petroleum hydrocarbon. This is particularly true of the more sustainable remediation treatment techniques.

In addition, causing an environmental contamination event can be considered as a serious offence with hefty penalties applicable to entities that flagrantly cause serious contamination. In these instances, regulators must rely on time-intensive and costly techniques to monitor the contamination event, with the delay in testing time, in turn, causing a delay in possible action to control the severity of the event.

Such testing situations typically involve the testing of numerous soil samples involving the extraction and quantification of contaminant components, which is generally time consuming and labour intensive. For example, for the analysis of total petroleum hydrocarbons (TPHs) in soil, testing is usually carried put via supercritical fluid extraction of the TPH components from the soil samples followed by the quantitative analysis of the TPH either by gas chromatography-flame ionisation detection (GC-FID) and/or gas chromatography-mass spectrometry (GC-MS). GC-MS is particularly suitable for the quantitative analysis of the more volatile components of TPHs (ie compounds in the C6 to C10 carbon chain range), but often utilises a purge and trap method where a heated purge gas is used to introduce the TPH components to the GC column; a procedure that, alone, may take up to twenty minutes per sample. For the less volatile components of TPH (ie compounds in the C10 to C36 range), detection in soil or sediment samples can potentially be achieved by the direct extraction of the contaminants using a solvent such as methylene chloride, following sample sonication, and introduction of the TPH components to a GC column for GC-MS analysis or analysis by Fourier Transform (FT) IR transmission (Sadler and Connell, 2003). However, these techniques, although they potentially provide accurate results, can be time consuming and labour intensive. Moreover, none of these methods, which necessarily involve the use of sensitive equipment, are particularly suited to the direct on-site analysis of contaminants such as petroleum hydrocarbon.

Accordingly, a rapid and/or simple method for detecting the presence of contaminants, and particularly TPH components, in a site could provide significant cost advantages (ie in terms of reduced testing costs and/or the avoidance of delays in test results leading to productivity losses), and/or other advantages of rapid response, such as the capacity to undertake preventative measures to prevent further contamination and/or to limit contaminant spread.

Infrared (IR) spectrometry techniques represent a possible alternative approach to supercritical fluid extraction and gas chromatography analyses of site contaminants. IR spectrometry distinguishes between chemical compounds by detecting the selective absorption of different IR wavelengths by chemical bonds; thus, every compound present in a sample being analysed, that is IR active, has a unique IR "spectral signature" enabling its identification and potential quantification. IR spectrometry-based techniques, such as diffuse reflectance infrared Fourier transform (DRIFT) spectroscopy with partial least-squares (PLS) chemometrics have been employed in agricultural soil analysis for the detection of organic carbon, exchangeable cations, air-dry moisture and clay content (Janik and Skjemstad, 1995; Reeves et al., 1999; and Cozzolino and Moron, 2003). For example, IR spectrometry has been used as a predictor of oil yield from oil shale minerals (Adams et al., 2005). However, these prior art techniques do not address the complexities associated with the qualitative or quantitative analysis of contaminants such as petroleum hydrocarbon in non-uniform and/or complex mixtures such as soil, sediment, rock or mineral samples. These difficulties arise because the spectral peaks typically attributable to petroleum hydrocarbon contaminants may also arise from the presence of naturally-occurring organic matter (NOM) and/or be masked by other factors in such non-uniform or complex samples. For example, using DRIFT, where the radiation penetrates only a short distance (a few tens of micrometers), quartz (as sand) and kaolinite clays can give particularly strong MIR spectral signatures which canvas a result, cause very weak spectral peaks to appear amplified while stronger spectral peaks may be distorted or disappear due to total "mirror" type of reflectance of the IR radiation.

The present invention is directed at IR spectrometry-based methods for detecting petroleum hydrocarbon contaminants in an environmental sample, particularly a soil, silt, sediment, rock, mineral or waste sample, which may overcome one or more of the problems associated with the prior art.

All publications, mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in any country before the priority date of each claim of this application.

SUMMARY

In a first aspect, the present invention provides for the use of an infrared (IR) signal in the range of 1360 $cm^{-1}$ to 2090 $cm^{-1}$ and/or 2650 $cm^{-1}$ to 3000 $cm^{-1}$ and/or 3700 $cm^{-1}$ to 4400 $cm^{-1}$, as an indicator of the presence of petroleum hydrocarbon.

In a second aspect, the present invention provides a method for the detection of petroleum hydrocarbon in a sample comprising the steps of:
 (i) subjecting the sample to infrared (IR) radiation, and
 (ii) detecting an IR signal in the range of 1360 $cm^{-1}$ to 2090 $cm^{-1}$ and/or 2650 $cm^{-1}$ to 3000 $cm^{-1}$ and/or 3700 $cm^{-1}$ to 4400 $cm^{-1}$;
wherein detection of said IR signal indicates the presence of petroleum hydrocarbon in said sample.

DETAILED DESCRIPTION

Figure 1:
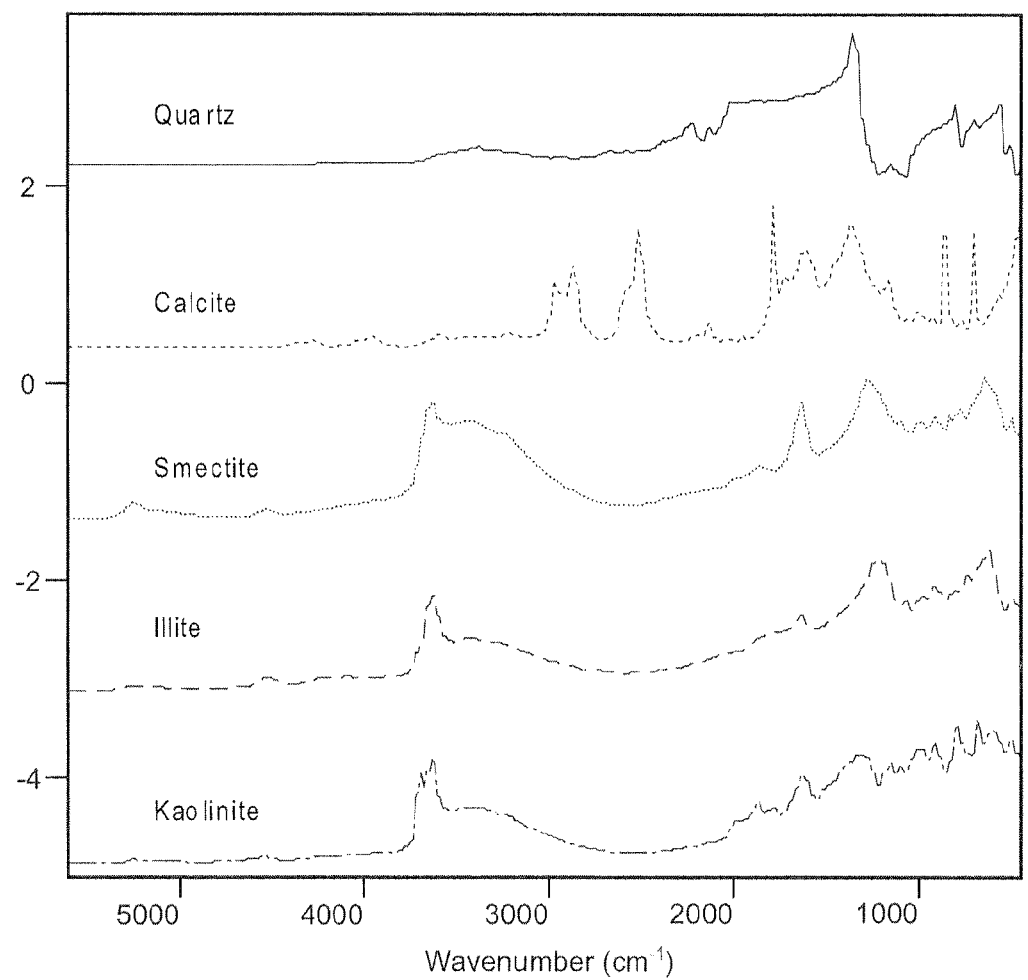
FIG. 1 shows the spectra of reference soil minerals, representing the most common soil minerals, by FT-IR spectroscopy. Arbitrary absorbance units are indicated on the y-axis and the frequency as wavenumber ($cm^{-1}$) is indicated on the x-axis.

Present methods for the detection of petroleum hydrocarbon in an environmental sample, such as a soil, silt, sediment, rock, mineral or waste sample, require the partial or complete extraction of the hydrocarbon compounds from the sample, which can be time consuming and labour intensive. It is therefore desirable that alternative methods be developed which allow for the detection of petroleum hydrocarbon directly from an environmental sample (ie such that extraction steps are avoided), however this is complicated by the typical presence of naturally-occurring materials such as NOM which may mask or hide characteristic signals of TPH components that might otherwise be useful for petroleum hydrocarbon detection. The present applicant has, however, identified previously unrecognised IR signals (eg characteristic IR absorption peaks) which can be used to indicate the presence of petroleum hydrocarbon in an environmental sample. The signals appear to be substantially unaffected by the presence, of similar chemical groups on other naturally-occurring materials that may commonly be found in environmental samples.

The IR signals that are identified herein as being useful in determining the presence of TPH are in the mid-infrared (MIR) and near-infrared (NIR) regions of the infrared spectrum and are attributed to fundamental, combination and overtone —C—H vibrations. This is in contrast to prior art techniques (eg. Zwariziger and Förster, 1998) that rely on spectra only acquired in the NIR region and, as such, rely only on overtones and combinations.

In a first broad aspect, the present invention provides for the use of an infrared (IR) signal in the range of 1360 $cm^{-1}$ to 2090 $cm^{-1}$ and/or 2650 $cm^{-1}$ to 3000 $cm^{-1}$ and/or 3700 $cm^{-1}$ to 4400 $cm^{-1}$ as an indicator of the presence of a petroleum hydrocarbon.

The term "petroleum hydrocarbon" as used herein in relation to an environmental sample, such as a soil, silt, sediment, rock, mineral or waste sample is to be understood to refer to substances comprising one or more hydrocarbon compounds considered to form a component of the group known as "total petroleum hydrocarbon" (TPH). Such substances include crude oil or substances derived from crude oil (eg petroleum products) and typically comprise C6 to C30 hydrocarbon compounds including a —$CH_3$ (methyl) terminus.

The term "infrared signal" or "IR signal" as used herein in relation to IR radiation or IR spectrometry of spectra, is to be understood to refer to any indicator of absorbance and/or reflection of IR radiation. For example, in IR spectroscopy, an IR signal may comprise an absorbance or reflection peak in the IR spectrum. Reference herein to an IR signal at a specific wavenumber (eg 2850 $cm^{-1}$) is intended to include many wavenumbers over a range, centred ion a signal at that particular wavenumber.

As used herein, all infrared intensities are expressed as absorbance units (A) wherein, A=Log Reflectance$^{-1}$ and all frequencies are expressed as wavenumbers ($cm^{-1}$).

Preferably, the use of the present invention is intended for the detection of petroleum hydrocarbon in an environmental sample such as a soil, silt, sediment, rock, mineral or waste sample.

Common soils, sediments, wastes or other environmental matrices often comprise naturally-occurring materials (NOMs) that may cause interference in performing IR spectrometry for petroleum hydrocarbon. In particular, these NOMs may mask or hide characteristic signals of petroleum hydrocarbon by, for example, giving a very strong IR signal that masks weaker IR signals (such as the weak IR absorption peak characteristic of TPH) or otherwise introduces "spectral noise" preventing the differentiation or identification of indicative peaks.

For instance, soil minerals can give strong IR signals in regions of the MIR and NIR; for example, strong IR absorption peaks below 2000 $cm^{-1}$, particularly in the region of 1100 $cm^{-1}$ and 1000 $cm^{-1}$, are apparent in soil samples comprising quartz (ie sand) and kaolinite clays due to the presence of silicate (—$SiO_2$) structures in these substances and the consequent Si—O stretching vibration. In addition, the presence of clays such as smectite, illite and kaolinite can cause a strong IR signal in the 3690 $cm^{-1}$ to 3620 $cm^{-1}$ region due to clay lattice Al—OH vibrations, and further, any water absorbed into the clay structures can result in the generation of broad IR absorption peaks in the region from 3500 $cm^{-1}$ to 3300 $cm^{-1}$. Moreover, the —OC—NH groups of any proteins that may be present in a sample create an IR signal near 1680 $cm^{-1}$ and 1530 $cm^{-1}$, while the presence of other types of NOM bearing carboxylate (COO—) groups or carboxyl (—COOH) groups can be apparent from strong IR signals (at 1600 $cm^{-1}$ and 1400 $cm^{-1}$ and near to 1720 $cm^{-1}$, respectively. Also, carbonate (—$CO_3$) groups, generate characteristic IR signals in the regions in and near 2980 $cm^{-1}$ to 2870 $cm^{-1}$, 2600 $cm^{-1}$ to 2500 $cm^{-1}$ and 1810 $cm^{-1}$, with the main —$CO_3$ peak apparent near 1375 $cm^{-1}$. These peaks overlap with several regions, mainly the 2900 $cm^{-1}$ to 2800 $cm^{-1}$ spectral region, where peaks resulting from the presence of alkyl groups (such as —$CH_3$ of petroleum hydrocarbon compounds) may also be found. For example, characteristic IR absorption peaks for alkyl groups are observed in the 2950 $cm^{-1}$ to 2850 $cm^{-1}$ region near 2955 $cm^{-1}$ (—$CH_3$), 2931 $cm^{-1}$ and 2856 $cm^{-1}$ (—$CH_2$) (corresponding overtone peaks for these vibrations can be seen in the NIR at 4388 $cm^{-1}$, 4329 $cm^{-1}$ and 4256 $cm^{-1}$), however due to the potential interference caused by strong IR signals from NOM-derived alkyl groups and/or carbonate groups, it has not been previously considered possible to use one or more peaks in these regions as a reliable indicator of the presence of petroleum hydrocarbon in complex mixtures such as soil.

The use of the present invention is based upon the surprising finding that petroleum hydrocarbon compounds generate characteristic IR signals at or near 1380 $cm^{-1}$, 2690 $cm^{-1}$, 2730 $cm^{-1}$, 2830 $cm^{-1}$, 2850 $cm^{-1}$, 2870 $cm^{-1}$, 2950 $cm^{-1}$, 4164 $cm^{-1}$, 4256 $cm^{-1}$, 4329 $cm^{-1}$ and/or 4388 $cm^1$, particularly signals at or near 2730 $cm^{-1}$, 2830 $cm^{-1}$, and 2870 $cm^{-1}$. These "TPH-sensitive peaks" can be used to detect TPH even in the presence of naturally-occurring materials commonly found in environmental samples such as soil samples which might otherwise have been expected to confound the detection of petroleum hydrocarbon by an IR spectrometry-based method. For example, these "TPH sensitive peaks" can be used in the presence of carbonate (—$CO_3$) peaks detectable in the 2600 $cm^{-1}$ to 2500 $cm^{-1}$ and 2980-2870 $cm^{-1}$. These carbonate signals partly overlap with TPH alkyl peaks in the 2950-2850 $cm^{-1}$ range.

However, as will be appreciated by persons skilled in the art, some variation in the exact location of the "TPH-sensitive peaks" can be anticipated depending upon, for example, the IR spectrometry equipment used and/or variation in the physical characteristics of the sample submitted for analysis. Indeed, many IR spectrometers may show some instability between scans of the same sample and nonetheless provide adequate stability for performing petroleum hydrocarbon analysis. Further, persons skilled in the art will recognise that some variation in the exact location of a reported peak will often be observed upon the repetition of IR analyses. Thus, the use of the present invention utilises specific IR signals in the mid-infrared (500-4000 $cm^{-1}$) and near-infrared ranges (4000-7500 $cm^{-1}$)

In some embodiments, the present invention utilises IR signals in the range of 2700 $cm^{-1}$ to 2950 $cm^{-1}$. In some embodiments, the present invention utilises IR signals in the range of 2690 $cm^{-1}$ to 2760 $cm^{-1}$, preferably in the range of 2710 $cm^{-1}$ to 2750 $cm^{-1}$. In specific embodiments, the use of the present invention utilises an IR signal at or near 2730 $cm^{-1}$.

In some other embodiments, the present invention utilises the an IR signal in the range of 2830 $cm^{-1}$ to 2870 $cm^{-1}$. In some embodiments, the invention utilises an IR signal in the range of 2810 $cm^{-1}$ to 2890 $cm^{-1}$, more preferably in the ranges 2810 $cm^{-1}$ to 2850 $cm^{-1}$ and/or 2850 $cm^{-1}$ to 2890 $cm^{-1}$. In some specific embodiments, the present invention utilises IR signals at or near 2830 $cm^{-1}$ and 2870 $cm^{-1}$. These signals are the wings of a peak at or near 2850 $cm^{-1}$ and, therefore, in some other embodiments, the use of the present invention utilises and IR signal over this range centred on a peak near 2850 $cm^{-1}$.

In some other embodiments, the present invention utilises an IR signal in the range of 2670 $cm^{-1}$ to 2710 $cm^{-1}$, more preferably in the range of 2680 $cm^{-1}$ to 2700 $cm^{-1}$. In specific embodiments, the use of the present invention utilises and IR signal at or near 2690 $cm^{-1}$.

In some other embodiments, the present invention utilises and IR signal in the range of 4150 $cm^{-1}$ to 4180 $cm^{-1}$, more preferably in the range of 4160 cm$^{-1}$ to 4170 cm$^{-1}$. In specific embodiments, the use of the present invention utilises and IR signal at or near 4164 cm$^{-1}$.

In some other embodiments, the present invention utilises at least one IR signal at or near 4256 cm$^{-1}$, 4329 cm$^{-1}$ and/or 4388 cm$^{-1}$.

The IR signals may be used alone or in combination to determine the TPH concentration in a sample. For example, we have found that for lower concentration ranges (eg. 0-1,500 mg/kg) use of the IR signals at or near 2830 cm$^{-1}$ and 2870 cm$^{-1}$ provides a model that is improved relative to the model obtained using only the IR signal at 2730 cm$^{-1}$ over the same concentration range.

In a second aspect, the present invention provides a method for the detection of petroleum hydrocarbon in a same comprising the steps of:
(i) subjecting the sample to infrared (IR) radiation; and
(ii) detecting an IR signal in the range of 1370 cm$^{-1}$ to 2090 cm$^{-1}$ and/or 2650 cm$^{-1}$ to 3000 cm$^{-1}$ and/or 3700 cm$^{-1}$ to 4400 cm$^{-1}$
wherein detection of said IR signal indicates the presence of petroleum hydrocarbon in said sample.

Preferably, step (i) comprises subjecting the same to IR radiation spanning almost the entire IR region of the electromagnetic spectrum (ie at least 450 cm$^{-1}$ to 7800 cm$^{-1}$). Alternatively, where, for example, the method utilises a portable or relatively basic IR spectroscopy equipment, it may be preferable to subject the sample to mid-infrared (MIR) radiation (ie 500 cm$^{-1}$ to 4000 cm$^{-1}$), or near-infrared (NIR) radiation (ie 4000 cm$^{-1}$ to 7800 cm$^{-1}$), or optionally a combination of MIR radiation and NIR radiation.

The methods described herein may find application, for instance, for the detection of petroleum tank leakage, particularly where tanks may be stored underground and wherein leakage detection presents a practical difficulty, and for the detection of petroleum hydrocarbons in dredge materials and other mixed wastes, such as industrial wastes.

The methods used herein may also find application in oil and gas exploration in which rapid detection of petroleum hydrocarbons in rock, mineral, silt or sand can be used as a rapid indicator of an area requiring further, detailed exploration.

Step (i) may be conducted directly on the sample (ie without any pre-processing or pre-treatment of the sample), however, for some samples such as soil, sediment, rock, mineral or waste samples, it may be preferred to crush or grind and/or sieve the sample prior to exposure to the IR radiation, so as to eliminate large particles and/or to ensure substantial uniformity in sample particle sizes. Further, for many solid samples, the surface characteristics of the particles within a sample may contribute to the "spectral definition" of the sample. If has, however, been found that if the sample is subjected to crushing or grinding, there can be a decrease in the baseline absorbance. Accordingly, for some samples, it may be preferred that before subjecting the sample to IR radiation, the sample is pre-processed to produce a sample comprising particles measuring less than 500 μm, more preferably, less than 200 μm, and most preferably, less than about 63 μm.

Further, it has been found that on certain particle surfaces, the presence of water or other solvents may "mirror" the IR radiation thereby causing distortion and/or the amplification of minor IR signals. Therefore, for some samples, it may be preferred, particularly when IR absorbance spectroscopy is used, to dry the sample prior to subjecting the sample to IR radiation. Drying the sample is preferably conducted in air at a temperature of less than 40° C. so as to avoid the volatilisation of modification of petroleum hydrocarbon. More preferably, the drying of the sample is conducted at ambient temperature.

Moreover, for some samples, it may be preferred to mix in a known amount of a diluent, such as an alkali halide (eg KBr) or fine clay, so as to achieve a substantially uniform baseline absorbance. It has been observed that the IR signal of petroleum hydrocarbon may be reduced by the presence of clay particles in the sample. It is suspected that clays and other porous media effectively shield the hydrocarbon from the IR radiation (which can only penetrate the sample to a depth of about 5 μm to 20 μm) through the absorption of the petroleum hydrocarbon within the solid particle. Soil particle size distribution may therefore need to be taken into consideration as a confounding factor.

In some embodiments, the IR signal to be detected in step (ii) is in the range of 2650 cm$^{-1}$ to 3000 cm$^{-1}$.

In some embodiments, the IR signal to be detected in step (ii) is in the range of 2700 cm$^{-1}$ to 2950 cm$^{-1}$, more preferably 2670 cm$^{-1}$ to 2780 cm$^{-1}$, more preferably still in the range of 2690 cm$^{-1}$ to 2760 cm$^{-1}$, and even more preferably still in the range of 2710 cm$^{-1}$ to 2750 cm$^{-1}$. Most preferably, the IR signal to be detected is at or near 2730 cm$^{-1}$. We have found that the IR signal at 2730 cm$^{-1}$ can be used across a wide range of TPH concentrations (eg from 0 to about 33,000 mg/kg).

In some embodiments, the IR signal to be detected in step (ii) is in the range of 2810 cm$^{-1}$ to 2890 cm$^{-1}$, more preferably in the ranges 2810 cm$^{-1}$ to 2850 cm$^{-1}$ and/or 2850 cm$^{-1}$ to 2890 cm$^{-1}$. Most preferably, the IR signal to be detected is at or near 2830 cm$^{-1}$ and/or 2870 cm$^{-1}$.

In some embodiments, the IR signal to be detected in step (ii) is at or near 2950 cm$^{-1}$.

In some other embodiments, the IR signal to be detected in step (ii) is in the range of 1360 cm$^{-1}$ to 2090 cm$^{-1}$, more preferably in the ranges 1360 cm$^{-1}$ to 2000 cm$^{-1}$. Most preferably, the IR signal to be detected is at or near 1380 cm$^{-1}$.

In some other embodiments, the IR signal to be detected in step (ii) is in the range of 2670 cm$^{-1}$ to 2710 cm$^{-1}$, more preferably in the range 2680 cm$^{-1}$ to 2700 cm$^{-1}$. Most preferably, the IR signal to be detected is at or near 2690 cm$^{-1}$.

In some other embodiments, the IR signal to be detected in step (ii) is in the range of 4150 cm$^{-1}$ to 4180 cm$^{-1}$, more preferably in the range 4160 cm$^{-1}$ to 4170 cm$^{-1}$. Most preferably, the IR signal to be detected is at or near 4164 cm$^{-1}$.

The method of the present invention may be performed using, standard IR spectroscopy apparatus. Further, the scanning methodology utilised in the standard IR spectroscopy apparatus may be optimised for use with the method of the present invention by, for example, adjusting the scanning duration and resolution (eg optimised methods may involve scanning for 60 seconds in the range from 4000 cm$^{-1}$ to 500 cm$^{-1}$ (2500 nm to 20000 nm) at a resolution of 8 cm$^{-1}$, followed by repeat scans adjusted for a frequency and/or resolution above and/or below these values). Optimisation of the scanning methodology may also involve carrying out background reference scans, for instance, using silicon carbide (SiC) discs, gold or potassium bromide (KBr) designated with a reflectivity of 1. Advantageously, the method of the present invention may be performed using a portable DRIFT MIR spectrometer, optionally with some limited NIR capabilities included. A portable DRIFT MIR spectrometer may be used for in-situ scanning of soils. We have found that spectra obtained using a hand-held DRIFT MIR spectrometer are very similar to spectra obtained using lab-based instruments. As such, the method of the present invention may be used to rapidly generate data and, potentially, produce a spatial map of the soil TPH content over an area.

In embodiments comprising detecting an IR signal in the range of 2700 cm$^{-1}$ to 2760 cm$^{-1}$, the method may further comprise:
(iii) detecting an additional IR signal in the range of 1000 cm$^{-1}$ to 2700 cm$^{-1}$ and/or 2760 cm$^{-1}$ to 6000 cm$^{-1}$.

The identification of the additional IR signal may provide a stronger indication of the presence of petroleum hydrocarbon in the sample. For example, —CH$_3$ IR absorption peaks in range of 2845 cm$^{-1}$ to 2965 cm$^{-1}$, their overtone peaks in the 4375 cm$^{-1}$ to 4395 cm$^{-1}$ range and/or the 5860 cm$^{-1}$ to 5875 cm$^{-1}$ range, or their deformational peaks in the 1355 cm$^{-1}$ to 1395 cm$^{-1}$ range may be used to confirm the 2700 cm$^{-1}$ to 2760 cm$^{-1}$ IR signal, as may the 2730 cm$^{-1}$ overtone peak in the 2650 cm$^{-1}$ to 2700 cm range and/or the 3700 cm$^{-1}$ to 4400 cm$^{-1}$ range. These signals may be used in combination with the 2700 cm$^{-1}$ to 2750 cm$^{-1}$ IR signal, for instance, to provide a benchmark for providing a semi-quantitative assessment of TPH. Alternatively, they may be used to normalise the 2700 cm$^{-1}$ to 2760 cm$^{-1}$ IR signal. Further, ethyl (—CH$_2$CH$_3$) IR absorption peaks in the 2930 cm$^{-1}$ to 2845 cm$^{-1}$ range and/or 2845 cm$^{-1}$ to 2865 cm$^{-1}$ range and/or their overtone peaks in the 4245 cm$^{-1}$ to 4265 cm$^{-1}$, 4320 cm$^{-1}$ to 4340 cm$^{-1}$, 4345 cm$^{-1}$ to 4365 cm$^{-1}$, 5685 cm$^{-1}$ to 5695 cm$^{-1}$, 4295 cm$^{-1}$ to 4305 cm$^{-1}$ and/or 5795 cm$^{-1}$ to 5805 cm$^{-1}$ ranges, may also be used to, for example, account for the effect of NOM. Further, the main —CO$_3$ IR absorption peak in the 1370 cm$^{-1}$ to 1380 cm$^{-1}$ range, and/or its overtone peaks in the 1805 cm$^{-1}$ to 1810 cm$^{-1}$ range, the 2600 cm$^{-1}$ to 2500 cm$^{-1}$ range, and/or the 2980 cm$^{-1}$ to 2870 cm$^{-1}$ range, may be used to eliminate the interference.

The method of the present invention may be suitable for the detection of petroleum hydrocarbon in a liquid or aqueous sample (ie without the need to dry the sample to a solid form). This can be achieved by, for example, utilising mirror reflection techniques (ie transflectance techniques) to overcome the difficulty of specular reflectance distortions that may otherwise be experienced using DRIFT. Thus, for example, the detection of petroleum hydrocarbon in materials in wet or damp conditions, need not be delayed by the requirement to transport samples off-site for drying.

The method of the present invention may also be suitable for providing a semi-quantitative assessment of TPH in a sample. For example, the method may be operated so as to provide an indication of the presence or absence of TPH above or below a significant threshold point. That is, the method may be operated to provide an assessment of whether a sample includes TPH at a level above or below a regulatory limit (eg. 10,000 mg/kg or parts per million by weight of TPH). This may be achieved by for example, including step (iii) in the method. The assessment may be achieved using, for example, software to aid in the automation of TPH determination (eg to perform a calculation of whether a sample includes TPH at a level above or below a significant threshold point). Further, such software may be used to combine data from IR signals in the 2700 cm$^{-1}$ to 2760 cm$^{-1}$ range with those in the 1000 cm$^{-1}$ to 2700 cm$^{-1}$ and/or 2760 cm$^{-1}$ to 6000 cm$^{-1}$ ranges.

For instance, in the treatment of petroleum hydrocarbon contaminated soils, existing techniques that are used to monitor the progress of treatment (such as GC techniques) require that samples be prepared off-site and prior to analysis, usually by time consuming and lengthy solvent extraction processes. Further, analyses must be performed on a representative number of samples from the site. The process of monitoring petroleum hydrocarbon treatment or remediation efforts can be a time consuming and expensive process with delays in analysis, in turn, causing costly delays in site redevelopment (eg. contracting equipment on standby while awaiting analytical results) or re-use (eg. lost income from residential tenants).

In addition, techniques such as GC analysis do not differentiate between NOM content, which is normally present at a concentration of <5% in Australian soils and sediments (Rayment & Higginson, 1992), from total petroleum hydrocarbon content. Therefore, it is probable that many previous false positive results have resulted in conducting unnecessary petroleum hydrocarbon treatment measures whilst delaying site redevelopment.

Further, false positive results may be observed in the detection of NOM from interference by TPH in measured samples. Thus, the present methods for detecting petroleum hydrocarbon in a sample may be used to improve current IR methods for the dejection of NOM in samples, particularly for NOM analysis in agricultural applications. The present methods may be used to reduce or eliminate interference from current methods which fail to distinguish between TPH and NOM, or the "TPH specific" signal may be combined with known NOM analyses, such as known IR analyses, to more accurately predict NOM content in a sample.

Similarly, the present methods for the rapid, on-site and/or specific detection of petroleum hydrocarbons may be applied in other settings, such as oil or petroleum exploration. Detritus is a common source of NOM frequently found in substantial amounts in the vicinity of oil or petroleum reservoirs. The presence of detritic films on the surface of core samples taken for the purpose of oil or petroleum exploration pose significant difficulties in the specific detection of petroleum hydrocarbon by conventional techniques, such as GC techniques. Thus, the present methods may provide for the rapid and/or specific detection of petroleum hydrocarbon for the characterisation of a core sample.

Thus, in the present methods the sample may be a core sample. Methods for extracting core samples from environmental matrices such as soil, sediment or rock in terrestrial or aquatic environments, are well known in the art. The core sample may be directly subjected to IR radiation, for instance an IR beam may scan the entire length or circumference of the exterior surface of a core sample or an IR beam may scan one or more specific sections of the core sample. For instance, a scan may be taken at 10 cm intervals along the length of the core sample.

Alternatively, the core sample or a portion thereof may be subjected to crushing or grinding. Crushed or ground samples may, optionally, be sieved. The core sample or a portion thereof may be pre-processed to comprise particles measuring less than 500 μm, more preferably, less than 200 μm, and most preferably, less than about 63 μm.

The present methods may therefore be used for identifying the location of oil or petroleum hydrocarbon reservoirs and/or characterising the oil or petroleum reservoirs of a known location.

The present methods may be integrated into a detection apparatus specifically adapted for the detection of petroleum hydrocarbon in environmental matrices. That is, the detection apparatus may be a handheld device suitable for performing petroleum hydrocarbon detection in-situ, ie without the need to remove the sample from the site, or alternatively, it may be a portable device suitable for the ex-situ detection of petroleum hydrocarbons on-site, for instance in a mobile laboratory. The detection apparatus may be adapted for on-site applications by miniaturisation and/or stabilisation of the spectrometer. This may be achieved, for example, by limiting the source of IR radiation in a detection apparatus to the transmission of IR radiation in a limited range comprising the 1360 cm$^{-1}$ to 2090 cm$^{-1}$ and/or 2650 cm$^{-1}$ to 3000 cm$^1$, and/or the 3700 cm$^1$ to 4400 cm$^{-1}$ range and/or by limiting the detection or an IR signal to a limited range comprising the 2650 cm$^{-1}$ to 3000 cm$^{-1}$ and/or 3700 cm$^{-1}$ to 4400 cm$^{-1}$ ranges.

Further, a detection apparatus adapted for the detection of petroleum hydrocarbon in environmental matrices may comprise software and hardware required to perform an analysis of the IR signal and to make a determination as to the presence and/or absence of petroleum hydrocarbon within predetermined confidence limits. The analysis may, optionally, comprise the software and hardware required to perform a semi-quantitative analysis. This may be used to determine whether the sample exceeds a predetermined threshold limit, for example the threshold may be set at a regulatory limit (eg 10,000 mg/kg TPH) to indicate whether the sample falls above or below the acceptable limit. A detection apparatus of this type has many applications, including for in-soil leak detection around tanks and pipes.

The present invention is hereafter further described by way of the following non-limiting examples and accompanying figures.

EXAMPLES

Example 1

Materials and Methods

Reference Soil Minerals

Sand (K140), bentonite (STX-T), kaolinite (Ballclay), illite (Tumut) and limestone (calcium carbonate—Univar) were sourced from an in-house minerals collection for the following hydrocarbon sorption analyses. The reference soil minerals were characterised by Rayment and Higginson, (1992) as shown in Table 1.

Particle Size Separation

Sand was dry sieved to 1000 μm-600 μm, 600 μm-500 μm, 500 μm-300 μm, 300 μm-212 μm, 212 μm-106 μm and 106 μm-63 μm to study the effects of particle size. Mixtures of smectite and sand were prepared in ratios of pure smectite to sand of 4:1, 1.5:1, 0.67:1, and 0.25:1.

Petroleum Hydrocarbon Stock Solutions

Two stock solutions of petroleum hydrocarbons were prepared from crude oil (Light crude blend, BP oil refinery, Kwinna, Wash., Australia) and diesel (Navy diesel, BP oil refinery, Kwinna) dissolved in cyclohexane (Merck). For sand sorption studies, a 10% stock solution of crude oil and diesel were prepared from 10 mL petroleum hydrocarbons in cyclohexane to give a total volume of 100 mL. A more dilute stock solution of 2.5% petroleum hydrocarbons in cyclohexane to a total volume of 100 mL was used for sorption experiments with clays. Diluted aliquots of the petroleum hydrocarbons stock solution (0 to 100%) were prepared from 0.00 mL, 0.05 mL, 0.10 mL, 0.25 mL, 1.00 mL, 2.00 mL, 2.50 mL, 5.00 mL, 7.50 mL, 10.00 mL and 20.00 mL of petroleum hydrocarbons stock in cyclohexane to give a 10 mL total volume of each aliquot.

Preparation of Mock Contaminated Samples

The diluted aliquots of the petroleum hydrocarbons stock solution were mixed with fixed weights of each soil mineral sample (ie 10 g for sand and 2.5 g for the clays) in a tumbler for 12 hrs to ensure an even dispersion of petroleum hydrocarbons throughout the sample particles. Samples were allowed to dry for 18 hrs at 40° C. in order to remove all traces of the cyclohexane solvent. The volatility of the crude oil was minimal at this temperature, with a loss of only 2% of volume at 40° C. over 24 hrs. Fixed weights of sand, comprising a wide range of particle sizes, and varying mixtures of sand and smectite were prepared and mixed with known amounts of diesel.

TABLE 1

Reference soil minerals characterised by standard methods (Rayment and Higginson, 1992)

| | | Particle Density | C and N | | | | |
|---|---|---|---|---|---|---|---|
| Clay type | Clay Name | g/cm3 | Total C % | CaCO3 % | Inorg C % | Org C % | Total N % |
| Kaolinte | Ballclay | 2.72 | 0.14 | 0.26 | 0.03 | 0.11 | 0.06 |
| Illite | Tumut | 2.83 | 0.07 | 0.17 | 0.02 | 0.05 | 0.01 |
| Smectite | STX-1 | 2.65 | 0.02 | 0.24 | 0.03 | −0.01 | 0.01 |
| Quartz | K140 Sand | 2.63 | 0.01 | 0.00 | 0.00 | 0.01 | <0.005 |

| | Exchangeable cations (pH 7) | | | | | | Total CEC determined with NH4 | | |
|---|---|---|---|---|---|---|---|---|---|
| Clay type | Ca (cmol+/kg) | Mg (cmol+/kg) | Na (cmol+/kg) | K (cmol+/kg) | Total (cmol+/kg) | ECaP (Ca/SumI) | ESP (Na/Sum) | (NH4) (cmol+/kg) | ECaP (Ca/Total) | ESP (Na/Total) |
| Kaolinte | 16.9 | 1.2 | 0.1 | 0.2 | 18.5 | 0.92 | 0.01 | 15.0 | 1.13 | 0.01 |
| Illite | 9.3 | 1.1 | 0.1 | 0.6 | 11.2 | 0.84 | 0.01 | 11.5 | 0.81 | 0.01 |
| Smectite | 50.2 | 16.8 | 7.5 | 0.2 | 74.6 | 0.67 | 0.10 | 72.6 | 0.69 | 0.10 |
| Quartz | | | | | | | | | | |

| | Exchangeable cations (pH 8.5) | | | | | | Total CEC determined with NH4 | | |
|---|---|---|---|---|---|---|---|---|---|
| Clay type | Ca (cmol+/kg) | Mg (cmol+/kg) | Na (cmol+/kg) | K (cmol+/kg) | Total (cmol+/kg) | ECaP (Ca/SumI) | ESP (Na/Sum) | (NH4) (cmol+/kg) | ECaP (Ca/Total) | ESP (Na/Total) |
| Kaolinte | 14.0 | 0.9 | 0.1 | 0.2 | 15.2 | 0.92 | 0.01 | 14.9 | 0.94 | 0.01 |
| Illite | 9.2 | 1.0 | 0.2 | 0.8 | 11.1 | 0.83 | 0.01 | 12.4 | 0.74 | 0.01 |
| Smectite | 50.3 | 15.0 | 7.1 | 0.3 | 72.5 | 0.69 | 0.10 | 85.6 | 0.59 | 0.08 |
| Quartz | | | | | | | | | | |

Spectroscopy (i) Mid-Infrared (MIR) Spectroscopy

MIR diffuse reflectance spectra were scanned using a Perkin-Elmer Spectrum-One Fourier transform mid-infrared (FT-MIR) spectrometer (Perkin Elmer Inc) on approximately 100 of soil. Spectra were scanned for 60 sec in the frequency (wavenumber) range 7800 $cm^{-1}$ to 450 $cm^{-1}$ (wavelength range 1280 nm-22000 nm) at a resolution of 8 $cm^{-1}$, with the near-infrared (NIR) region from 7800 $cm^{-1}$-4000 $cm^{-1}$ (1280 nm-2500 nm) and the MIR region from 4000 $cm^{-1}$ to 500 $cm^{-1}$ (2500 nm to 20000 nm). The spectrometer was equipped with an extended range KRr beam-splitter, a high intensity ceramic source, a deuterium triglycine-sulphate (DTGS) Peltier-cooled detector and a Pike "Auto-Diff" auto-sampling diffuse reflectance accessory. Spectra were expressed in absorbance (A) units (where A=Log $Reflectance^{-1}$). Background reference scans were carried out using silicon carbide (SiC discs—assumed to have a reflectivity of 1 (100%). Reference scans of crude oil and diesel were carried out by two reflectance methods as films deposited onto a mirror surface (transflectance) and also as applied to the surface of powdered KBr (DRIFT).

(ii) Near-Infrared (NIR) Dispersive Spectroscopy

Spectra were scanned using a FOSS NIRSystems 6500 Vis-NIR spectrometer (Foss NIRSystems, Silver Springs, Md., United States of America) consisting of a monochromator with a wavelength range of 400 nm-2500 nm and 2 nm intervals. Samples were placed "as received" into a quartz macro-sampling cuvette with an area of approximately 200 mm×25 mm and scanned in reflectance mode. Spectra were then converted into absorbance (A) units. Reference scans of crude oil and diesel were carried out by transmitting using a 1 mm quartz cuvette.

Chemometric Analysis

The full range of spectra was exported into Unscrambler™ Ver. 9.80 software (CAMO Technologies Inc, Woodbridge, N.J., United States of America), for chemometrics analysis. Principal components analysis (PGA) and Partial least squares (PLS) calibrations were carried out with the Unscrambler™ Ver. 9.80 software using full "leave-one-out" cross-validation (Geladi and Kowalski, 1986) PLS regression, and various pre-processing options, such as point to point baseline offset, to reduce the effects of non-systematic spectral baseline variance. This pre-processing captured the most relevant spectral information pertaining to the PLS analysis to develop robust and accurate regression models. Cross-validation regression statistics were expressed in terms of the coefficient of determination ($R^2$) and root mean square error of cross-validation (RMSECV). The detection limit was taken as the RMSEGV.

Results and Discussion

Spectra of Soil Minerals

Quartz (as sand) and kaolinite clays give particularly strong MIR spectral signatures near 1100-1000 $cm^{-1}$ (Si—O stretching vibration) and 3690-3620 $cm^{-1}$ (clay lattice Al—OH vibrations) respectively (Van der Marel and Beutelspacher, 1976; Janik et al., 1998; Reeves et al., 1999; and McCarty et al., 2002). Naturally-occurring organic matter (NOM), identified by spectral peaks due to alkyl —$CH_2$ at 2930-2850 $cm^{-1}$, protein amide —OC—NH near 1680 $cm^{-1}$ and 1530 $cm^{-1}$, carboxylate anion COO— at 1600 $cm^{-1}$ and 1400 $cm^{-1}$, and carboxylic acid —COOH near 1720 $cm^{-1}$ (Van der Marel and Beutelspacher, 1976; McCarty et al., 2002) can cause very strong interference with petroleum hydrocarbon alkyl peaks.

Soils and sediments generally comprise the mineral components of quartz (sand), kaolinite (non-hydrated 1:1 layer alumino-silicate clay), illite (potassium rich 2:1 layer alumino-silicate clays similar to mica) and smectite (hydrated 2:1 layer alumino-silicate clays with high cation exchange capacity). The spectra of these common minerals are shown in FIG. 1. Notably, peaks near 3600 $cm^{-1}$ are associated with Al—OH vibrations in clays such as smectite, illite and kaolinite, along with water absorbed into the clay structures showing broad peaks in the region 3500 $cm^{-1}$-3300 $cm^{-1}$. Quartz does not comprise any significant quantities of aluminium so the 3600 $cm^{-1}$ peaks are not observed, however, peaks below 2000 $cm^{-1}$ are apparent due to the silicate (—$SiO_2$) structure. Carbonate has characteristic peaks near 2980 $cm^{-1}$-2870 $cm^{-1}$, 2600 $cm^{-1}$-2500 $cm^{-1}$ and 1810 $cm^{-1}$, with the main —$CO_3$ fundamental peak near 1375 $cm^{-1}$. These carbonate peaks overlap with the region for the detection of alkyl compounds, mainly in the 2900 $cm^{-1}$-2800 $cm^{-1}$ spectral region. Therefore, the presence of carbonates in environmental matrices conceals the detection of peaks that correspond to the alkane types of total petroleum hydrocarbons (TPHs) such as diesel and crude oil.

FTIR Spectrum of Natural Organic Matter

Figure 2:
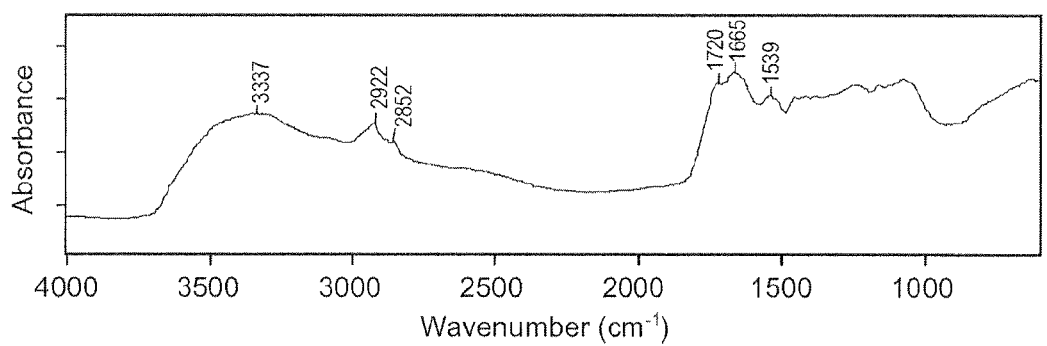
FIG. 2 shows the spectrum of NOM extracted from a reference soil sample.

Natural organic matter (NOM) is known to contribute <5% of the soil mass for Australian soils (Rayment & Higginson, 1992). FIG. 2 shows the spectrum of NOM extracted from soil. The peaks near 2922 $cm^{-1}$ and 2852 $cm^{-1}$ are due to the —$CH_2$ vibrations in alkyl structures from NOM, thought to result from lipids and other components of plant cell wall structures. While TPH compounds also form these alkyl peaks, the peaks predominantly reflect the presence of NOM; that is, there is little contribution to these peaks by —$CH_3$ terminal methyl groups present in TPH compounds.

Spectra of Crude Oil and Diesel

Figure 3:
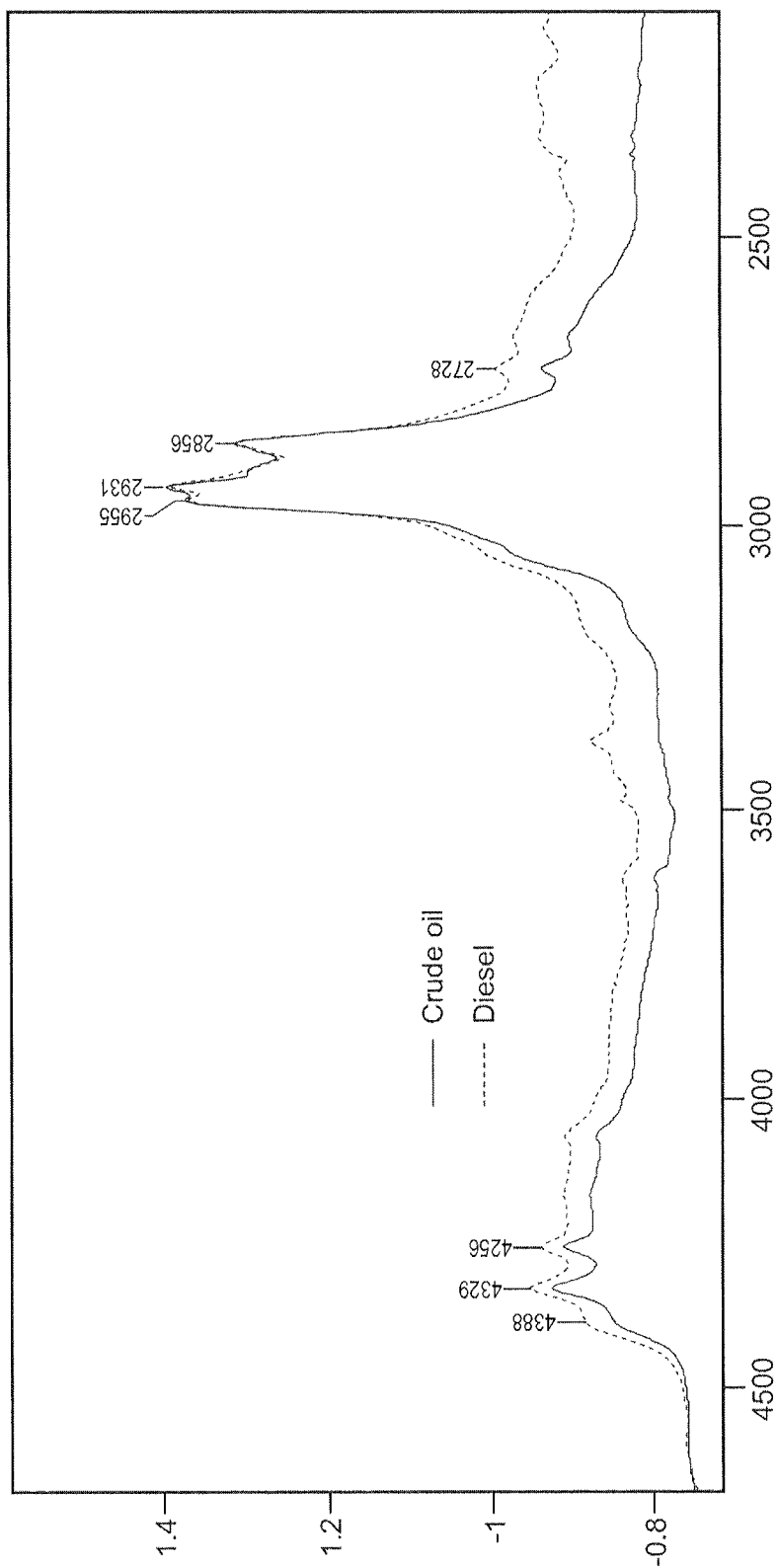
FIG. 3 shows regions of the FT-MIR (2500 $cm^{-1}$ to 4000 $cm^{-1}$) and FT-NIR (4000 $cm^{-1}$ to 5000 $cm^{-1}$) spectra of diesel and crude oil in sand. Diesel is shown by the broken and crude oil in the solid line.

FIG. 3 shows portions of the FT-MIR (2500 $cm^{-1}$-4000 $cm^{-1}$) and FT-NIR (4000 $cm^{-1}$-5000 $cm^{-1}$) spectra of diesel and crude oil in sand. Fundamental alkyl peaks are observed near 2955 $cm^{-1}$ (—$CH_3$), 2931 $cm^{-1}$ and 2856 $cm^{-1}$ (—$CH_2$). These are typical of peaks seen in the NIR for medium chain-length hydrocarbons. Corresponding overtone peaks for these vibrations can be seen in the NIR at 4388 $cm^{-1}$, 4329 $cm^{-1}$ and 4256 $cm^{-1}$. Since medium length alkanes, such as C15-C28 chain length diesel type of compounds, have a higher proportion of —$CH_3$ than NOM, it was hypothesised that the peaks attributed to —$CH_3$ may be predictive of TPH, even in the presence of NOM.

The Identification of TPH-Sensitive Peaks in the Infrared Spectra for TPH Prediction IR peak frequencies in the MIR at 2950 $cm^{-1}$, 2920 $cm^{-1}$, 2730 $cm^{-1}$ and 1380 $cm^{-1}$, peaks in the NIR and co-variate mineral peaks, particularly for quartz in the 1250 $cm^{-1}$-450 $cm^{-1}$ region were analysed for their suitability for TPH prediction. Two very small peaks had surprisingly and consistently been observed near 2730 $cm^{-1}$ and 2690 $cm^{-1}$ in the MIR spectra of diesel and crude oil. It was considered that these peaks, particularly the peak near 2730 $cm^{-1}$, may be due to the first overtone vibration of the —$CH_3$ symmetric deformation mode. The peak at 2730 $cm^{-1}$ may, therefore, be directly related to the TPH content in diesel and crude oil contaminated samples.

In order to confirm whether the 2730 $cm^{-1}$ peak could be used to determine the presence and/or concentration of hydrocarbons representing TPH, spectra scans of a number of hydrocarbons in the MIR and NIR region were carried out. MIR and NIR spectra were recorded using the FTIR described above as well as the NIRS6500 instrument for NIR analysis, as a comparison with the FT-NIR.

While the effect of NOM masking of TPH may be difficult to assess or quantify, the effect of NOM can be minimised by identifying IR peaks unique to TPH. Such peaks may represent extremely weak combination or overtone peaks of the fundamental —CH stretch and deformation vibrational modes specific to TPH, so that it may be that sense are sufficiently different to equivalent peaks to naturally occurring NOM to allow a differentiation of TPH from NOM alkyl peaks.

Six hydrocarbons, namely diesel, crude oil, n-hexane, iso-octane, chloro-hexadecane and n-octanol were scanned in three formats and on two spectrometers, namely Perkin-Elmer FTIR (FT-MIR and FT-NIR ranges) and FOSS NIRS6500 (visible and NIR spectral ranges), in order to identify —$CH_3$ specific spectral peaks and determine what effect there was on possible —$CH_3$ frequencies due to chain length and conformation. Sample formats included thin film on mirror (transflectance using MIR and NIR), liquid coatings on KBr powder particles (DRIFT in the MIR and NIR), and liquid cell (transmittance through the liquid hydrocarbon (NIRS6500)).

Figure 4A:
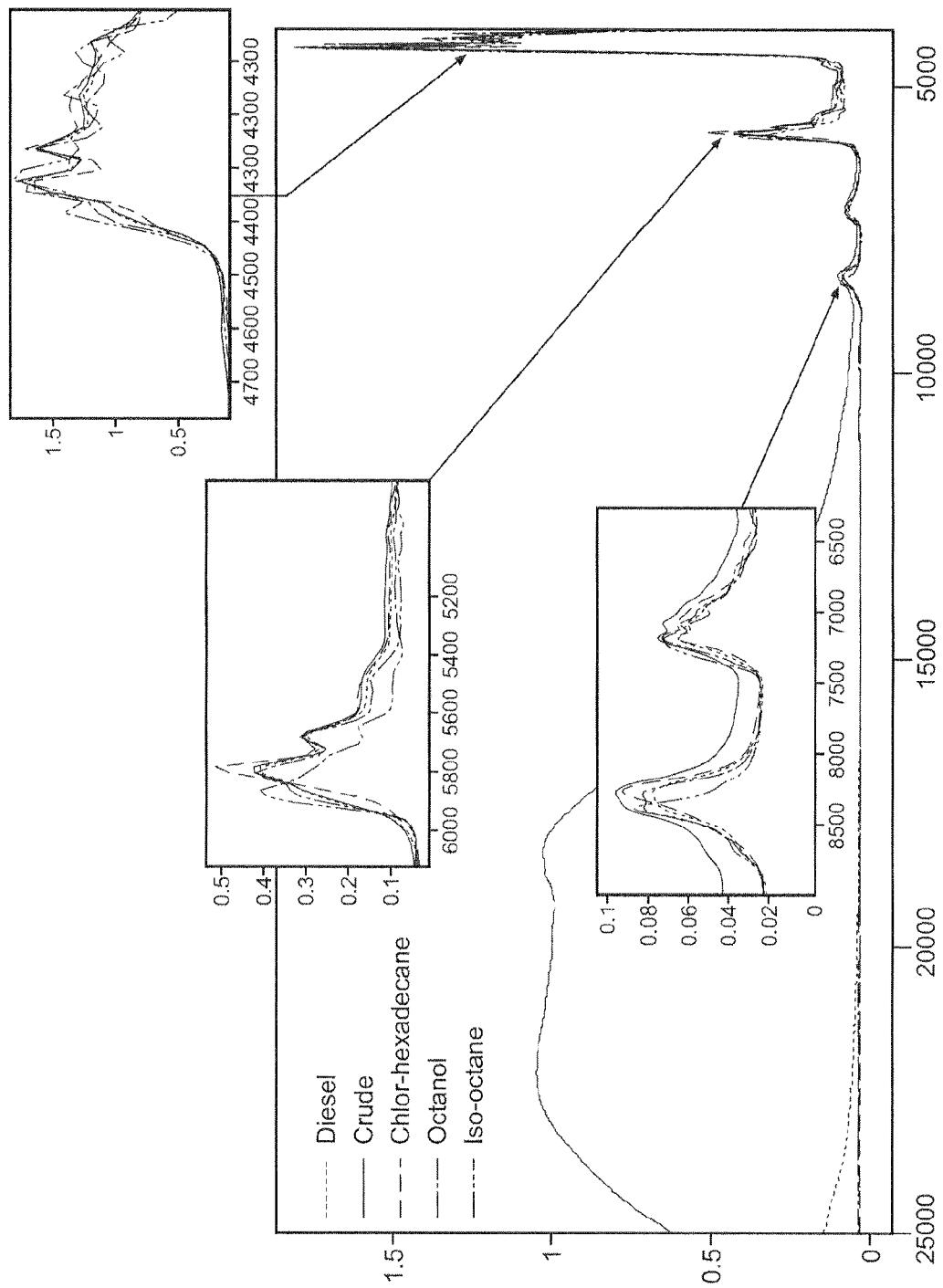
FIG. 4 (a): provides NIRS6500 vis-NIR transmittance spectra of hydrocarbon liquids (diesel, crude oil, n-hexane, iso-octane, chloro-hexadecane, and n-octanol) in a 1 mm quartz cuvette and (b): provides NIRS6500 vis-NIR transmittance (1 mm quartz cuvette) versus FT-NIR mirror (mirror transflectance) spectra of crude oil.

FIG. 4a depicts the visible NIR spectra of the alkanes using transmittance spectroscopy. Peaks due to —$CH_3$ were clearly observed at 4384 $cm^{-1}$, 5867 $cm^{-1}$ and 8387 $cm^{-1}$. Only one peak near 4164 $cm^{-1}$ was considered to be equivalent to the 2730 $cm^{-1}$ peak (ie close to the second overtone of the 1370 $cm^{-1}$—$CH_3$ peak). Other candidates could not be easily interpreted or observed due to insufficient signal or excessive spectral noise. Iso-octane and octanol showed peaks attributable to —$CH_3$ groups in agreement with the high ratio of —$CH_3$ to —$CH_2$ in these compounds, in contrast to chlorhexadecane which has a much lower ratio of —$CH_3$ to —$CH_2$ and consequently a smaller —$CH_3$ specific peak.

Figure 4B:
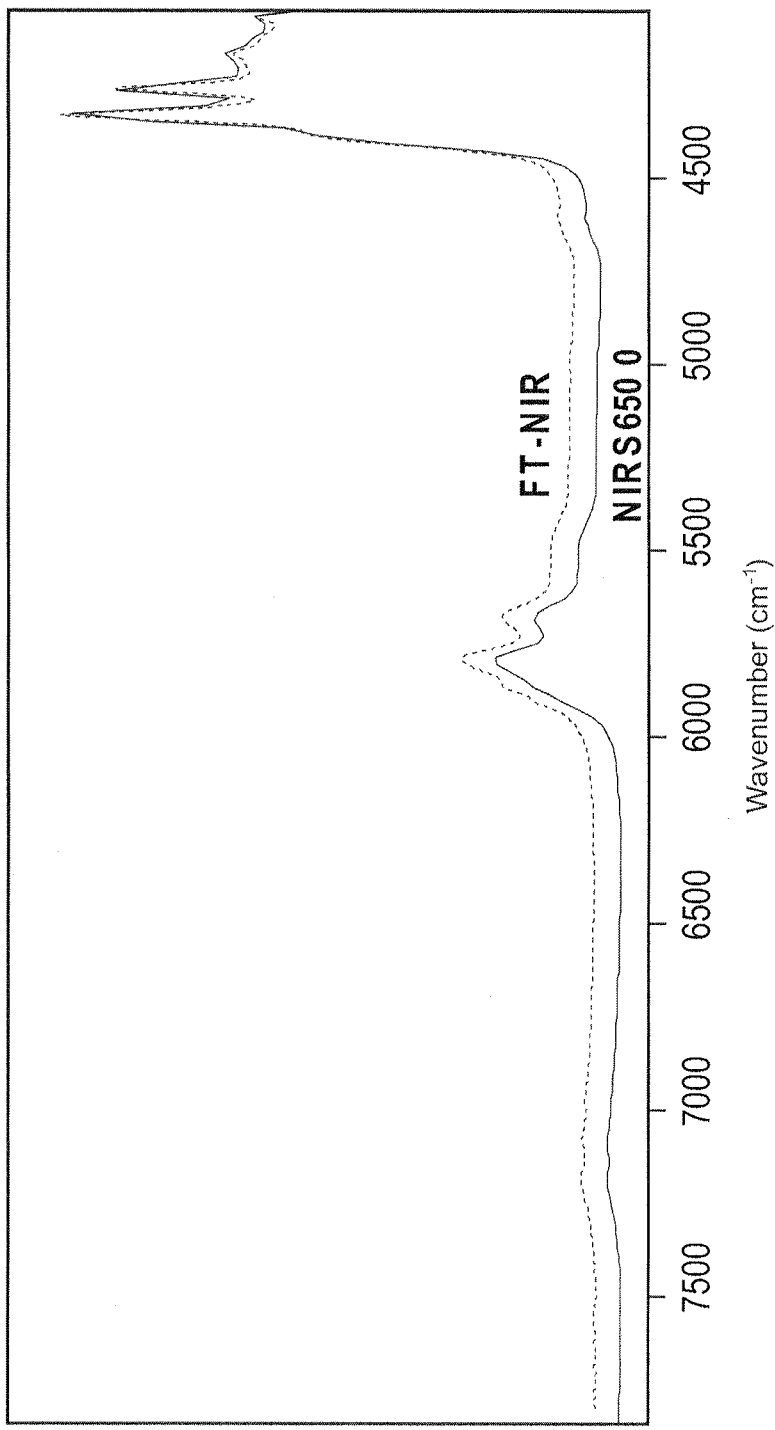

In order to identify the full range of peaks allocated to the —$CH_3$ species, the spectral range was extended into the MIR region. Difficulties were experienced in producing similar spectra with the FTIR spectrometer using the DRIFT technique due to specular reflectance distortions. It was however, possible to obtain similar spectra with the FTIR spectrometer using mirror reflection techniques (transflectance). FIG. 4b shows that a closely similar NIR spectrum can be obtained with FT-NIR by transflectance from a liquid sample deposited onto a mirror surface. It should therefore be possible to produce liquid spectra without the distortions inherent with the DRIFT technique right into the MIR region.

Figure 5:
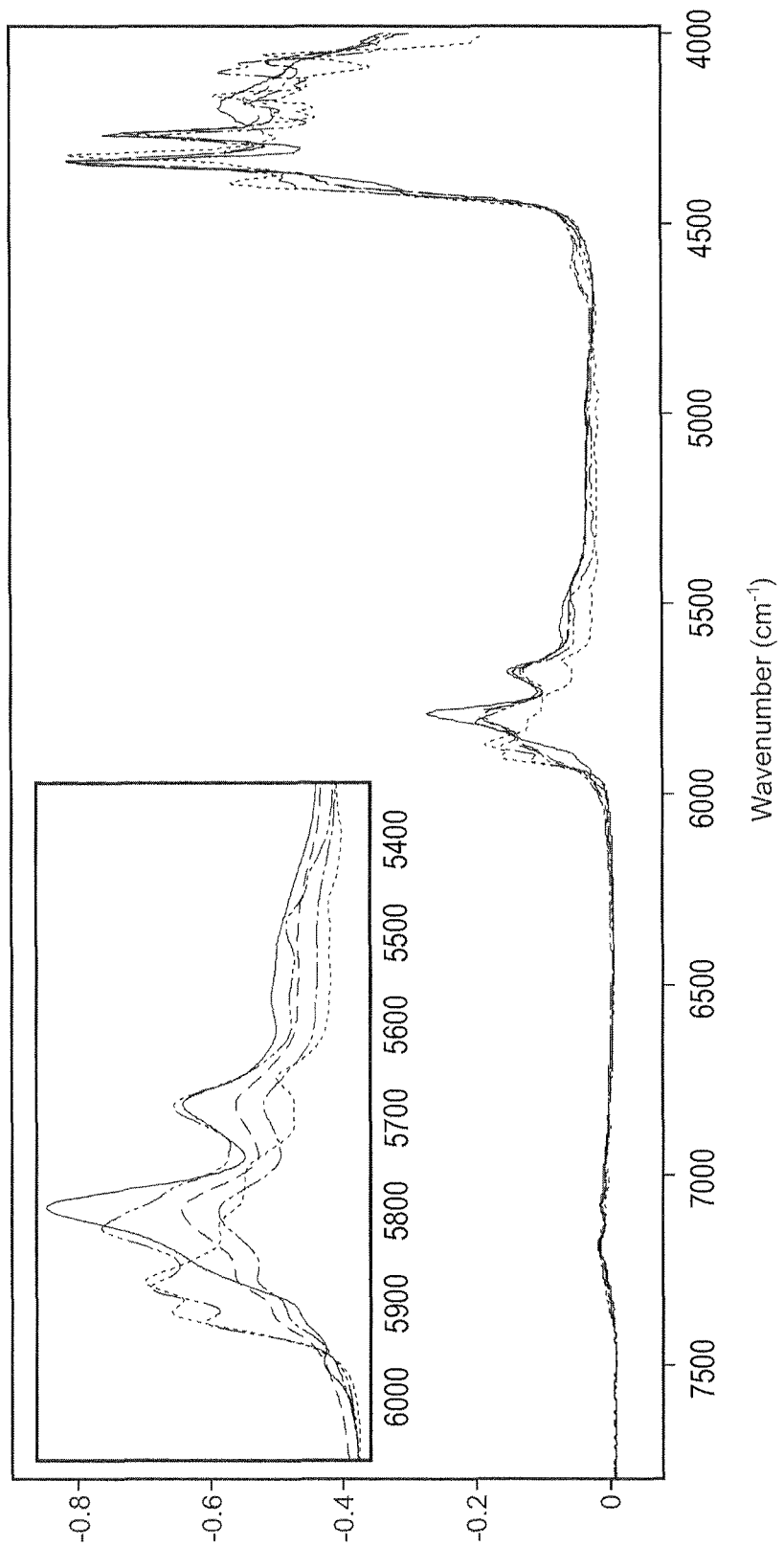
FIG. 5 provides FT-NIR mirror (mirror transflectance) spectra of hydrocarbon liquids (diesel, crude oil, n-hexane, iso-octane, chlororhexadecane, and n-octanol) in a 1 mm quartz cuvette. Insets show zoomed, spectral regions comprising alkyl peaks.
Figure 6:
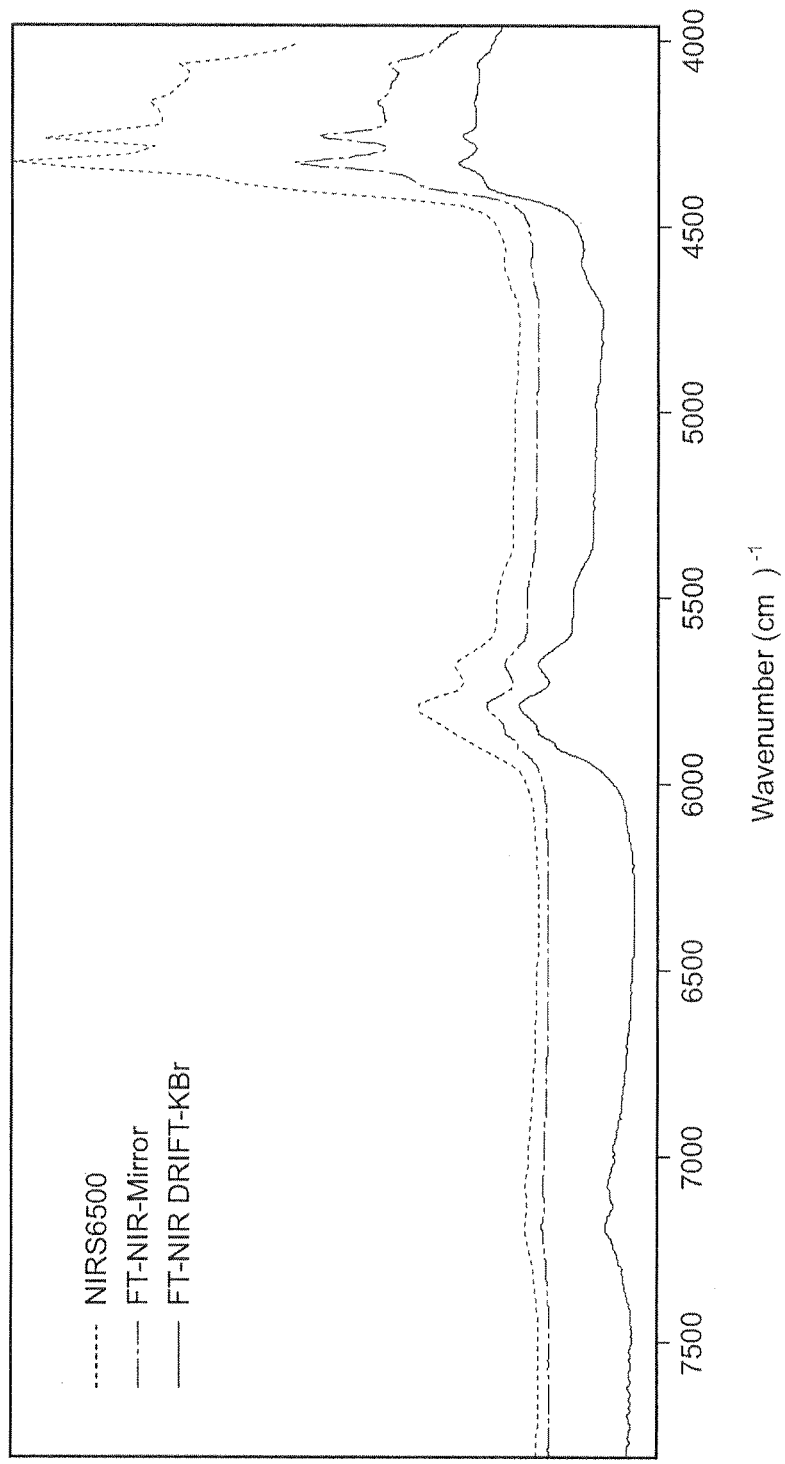
FIG. 6 shows a comparison of NIRS6500 vis-NIR transmittance (upper), FT-NIR mirror (transflectance) (middle) and FT-NIR DRIFT (lower) spectra of crude oil.

FIG. 5 depicts the spectra of the five alkanes scanned on the FTIR in the NIR spectral region using transflectance. The methyl —$CH_3$ peaks near 5867 $cm^{-1}$ and at 4384 $cm^{-1}$ are clearly differentiated from the alkyl —$CH_2$ peaks near 5800 $cm^{-1}$ and 5690 $cm^{-1}$ and near 4350 $cm^{-1}$ and 4400 $cm^{-1}$. DRIFT spectroscopy enabled the enhancement of relatively weak peaks, as shown in FIG. 6. For example, the peaks near 7200 $cm^{-1}$ were much stronger with DRIFT than with transmittance or transflectance. Conversely, the peaks near 4300 $cm^{-1}$ are much stronger with transmittance or transflectance. This technique permits the use of the very weak intensity peaks for chemometrics, such as the one at 2730 $cm^{-1}$.

The enhancement of weak peaks by DRIFT is even more apparent in the MIR spectrum. The DRIFT spectrum in FIG. 6 shows the increased intensity of the 2730 $cm^{-1}$, along with numerous other peaks previously not, or barely, observable by transmittance or transflectance. DRIFT MIR was therefore capable of amplifying weak peaks to provide the most detailed data for chemometric applications to, in turn, allow accurate TPH infrared predictions to be made.

Spectra of Crude Oil and Diesel Adsorbed into Minerals

The use of varying particle size sand samples was intended to show what effect, if any, there was on the reflection characteristics of TPH due to particle size. The use of varying proportions of sand and quartz mixtures was intended to show if there was any significant shielding of TPH reflection from quartz by the fine particle-size smectite.

Figure 7:
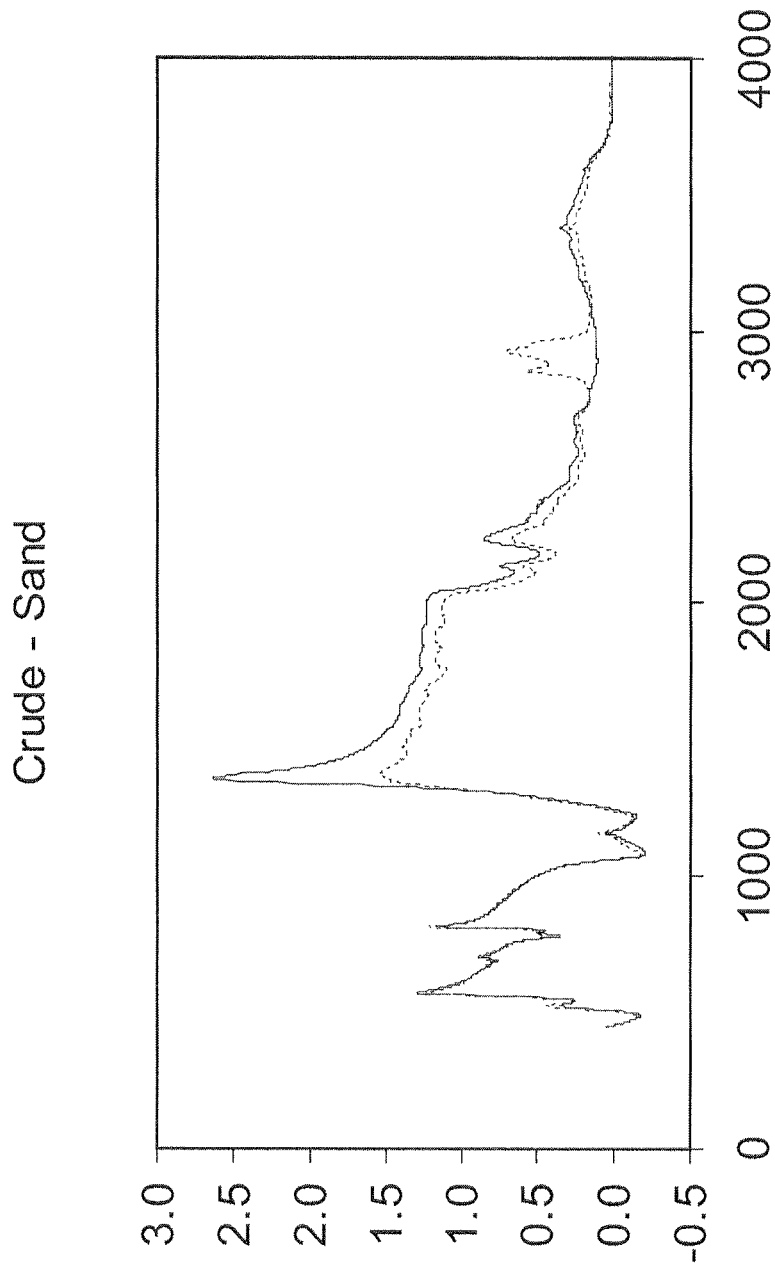
FIG. 7 shows the FT-MIR spectrum of sandy soil (solid line) and 1% crude oil adsorbed onto reference sandy soil (broken line)
Figure 8:
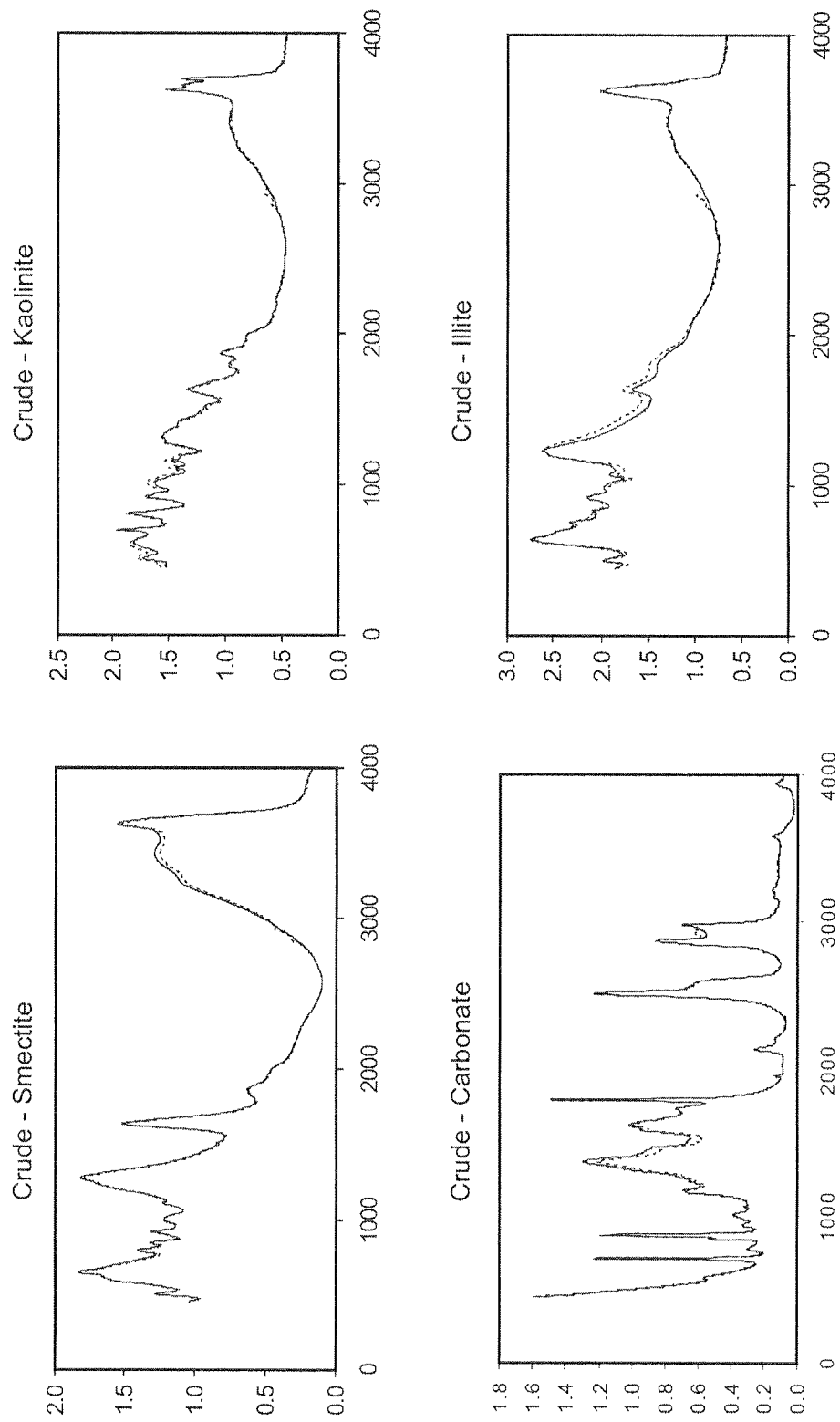
FIG. 8 shows the FT-MIR spectra of 1% crude oil adsorbed onto reference soils comprising (a) smectite, (b) kaolinite, (c) carbonate and (d) illite.
Figure 9:
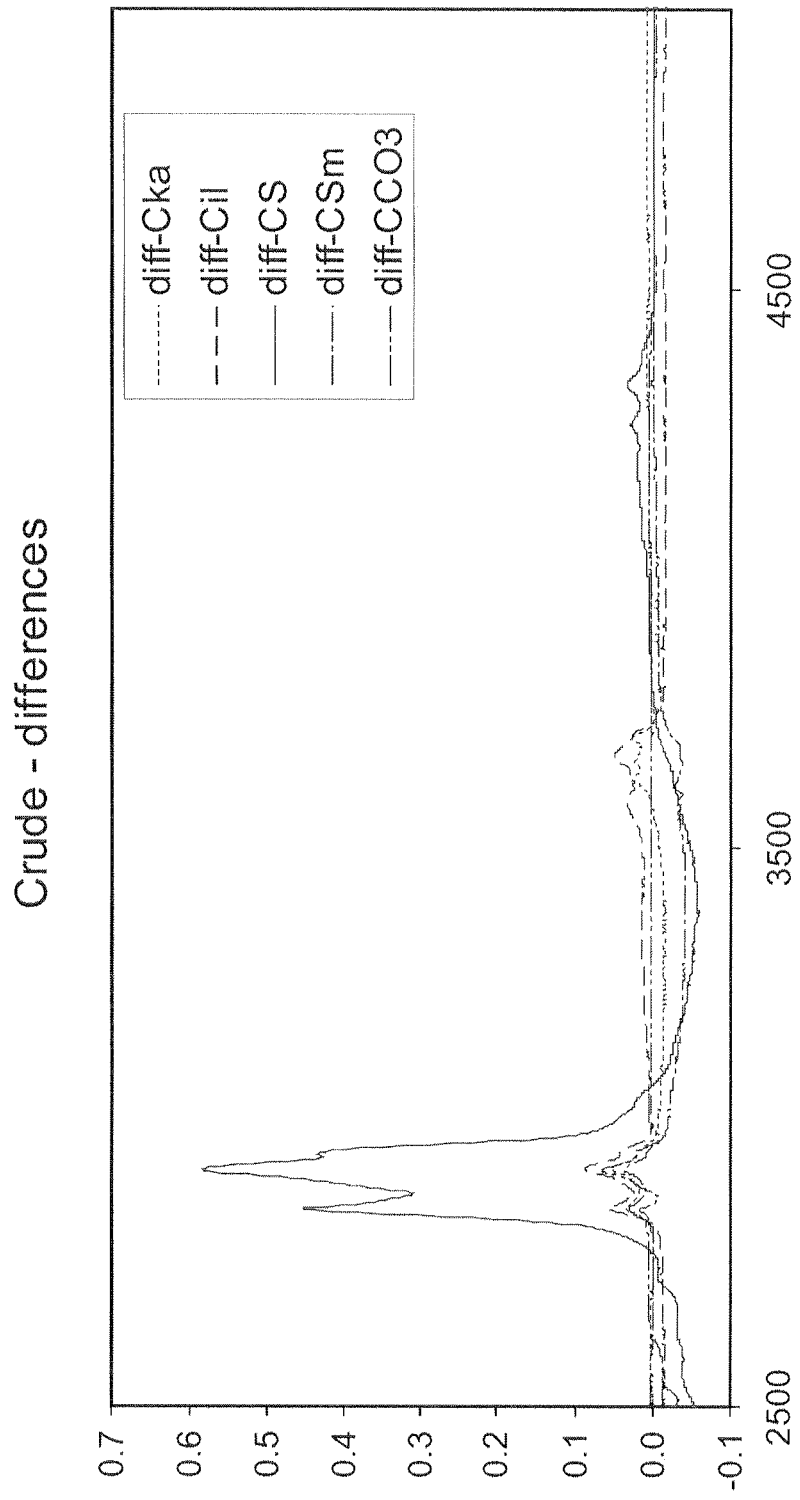
FIG. 9 shows a side-by-side comparison of the FT-IR spectra of crude oil adsorbed onto soil minerals from a 1% solution of crude oil in cyclohexane in the 2500 $cm^{-1}$ to 5000 $cm^{-1}$ range. Kaolinite is shown as diff-Cka, illite is shown as diff-Cil, sand is shown as diff-CS, smectite is shown as diff-Sm, and carbonate is shown as diff-$CCO_3$.

Sand adsorbs TPH and other coating materials as a film onto large, relatively smooth, surfaces. The IR reflection method "sees" this oil on the surface almost as a "transflectance" spectrum after reflection of the incident radiation through the TPH film and back again from the quartz particle surfaces. The spectrum of 1% crude oil adsorbed into sand is shown in FIG. 7, with alkyl peaks near 2950 $cm^{-1}$-2850 $cm^{-1}$ evident from the adsorbed crude oil. The FIG. 8 spectra show the absorption of 1% crude oil onto (a) smectite, (b) kaolinite, (c) carbonate, and (d) illite clay minerals. In contrast with sand, in smectite, illite, kaolinite and calcite clay minerals, petroleum hydrocarbons are absorbed into the internal structure of the particles rather than covering the sand particles as a film. As shown in FIG. 9, the crude oil alkyl peaks are stronger in sand than in the smectite, kaolin, carbonate and illite.

Given the contribution of particle surface characteristics to spectral detection, further studies were conducted to ascertain the effect of particle size on absorbance. Sand was progressively ground into finer particle sizes as shown in Table 3, with the spectra of progressively ground particles shown in FIG. 10.

TABLE 2

Diesel absorbed onto quartz of varying particle-sizes and sand/clay ratios

| Sample ID | Size range (μm) | stock diesel soln (mL) | hexane (mL) | Conc of diesel in hexane (mL/mL) | sample wt (g) | Conc diesel in sample (V/W %) |
|---|---|---|---|---|---|---|
| Q1 | 1000-600 | 1.00 | 9.00 | 0.025 | 2.524 | 0.98 |
| Q2 | 600-500 | 1.00 | 9.00 | 0.025 | 2.504 | 0.99 |
| Q3 | 500-300 | 1.00 | 9.00 | 0.025 | 2.503 | 0.99 |
| Q4 | 300-212 | 1.00 | 9.00 | 0.025 | 2.504 | 0.99 |
| Q5 | 212-106 | 1.00 | 9.00 | 0.025 | 2.508 | 0.99 |
| Q6 | 106-63 | 1.00 | 9.00 | 0.025 | 2.516 | 0.98 |

TABLE 3

Diesel absorbed onto smectite combined in varying sand/clay ratios

| Sample ID | Qu (g) | Sm (g) | Sample wt (g) | Stock diesel solution (mL) | Hexane (mL) | Conc of diesel in stock soln (mL/mL) | Conc diesel in sample (V/W %) |
|---|---|---|---|---|---|---|---|
| 1QS | 0 | 2.51 | 2.505 | 1.00 | 9.000 | 0.025 | 0.99 |
| 2QS | 0.502 | 2.00 | 2.504 | 1.00 | 9.000 | 0.025 | 0.99 |
| 3QS | 1.001 | 1.51 | 2.508 | 1.00 | 9.000 | 0.025 | 0.99 |
| 4QS | 1.505 | 1.01 | 2.518 | 1.00 | 9.000 | 0.025 | 0.98 |
| 5QS | 2.052 | 0.51 | 2.561 | 1.00 | 9.000 | 0.025 | 0.97 |
| 6QS | 2.524 | 0.00 | 2.524 | 1.00 | 9.000 | 0.025 | 0.98 |

Figure 10A:
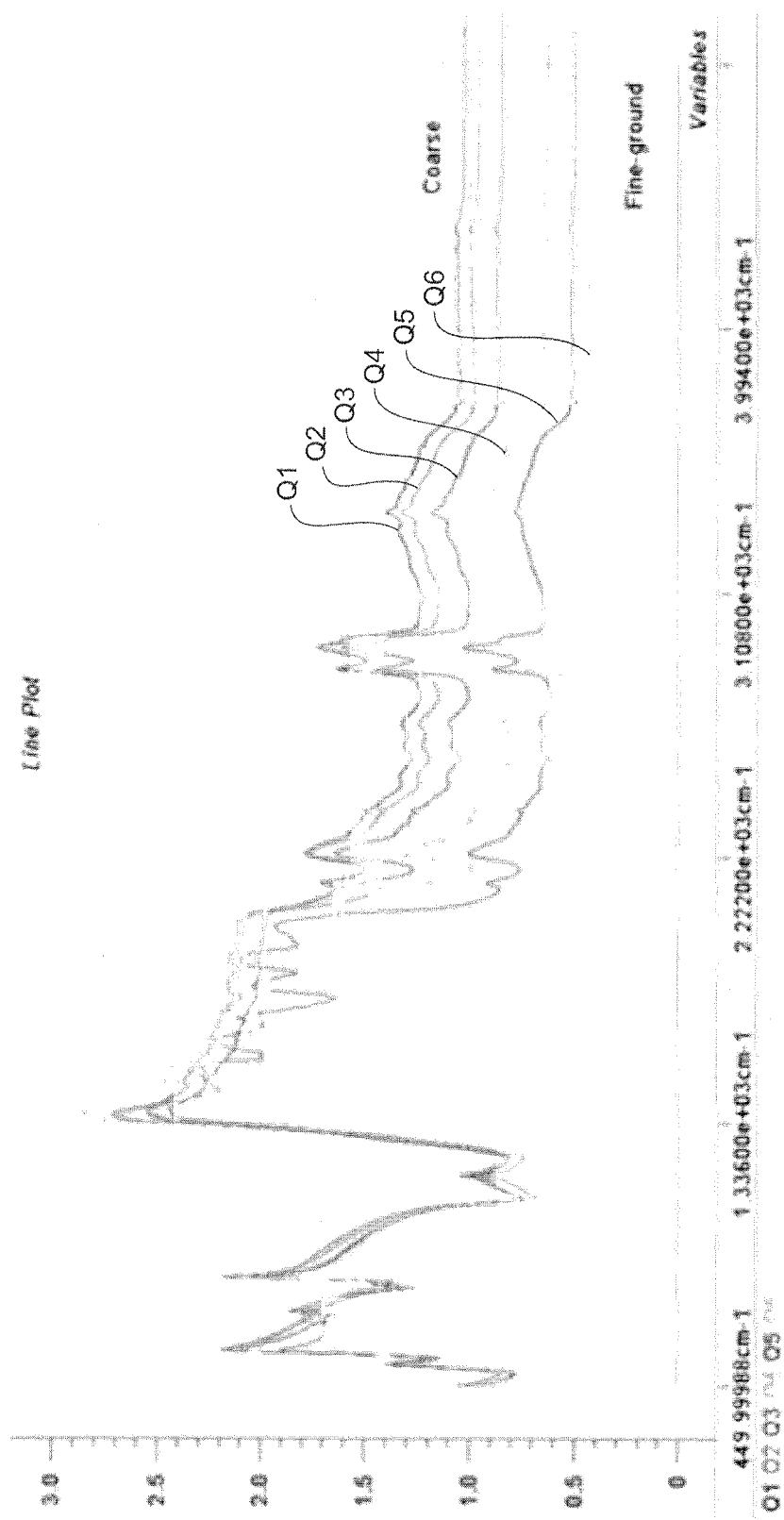
FIG. 10 shows the spectra of quartz particles of varying sizes with 1% diesel sorbed: (a) shows the spectra prior to correction and (b) shows the baseline corrected spectra of samples of 1000-600 μm diameter particle size (S1), 600-500 μm diameter particle size (S2), 500-300 μm diameter particle size (S3), 300-212 μm diameter particle size (S4), 212-106 μm diameter particle size (S5) and 106-63 μm diameter particle size (S6)
Figure 10B:
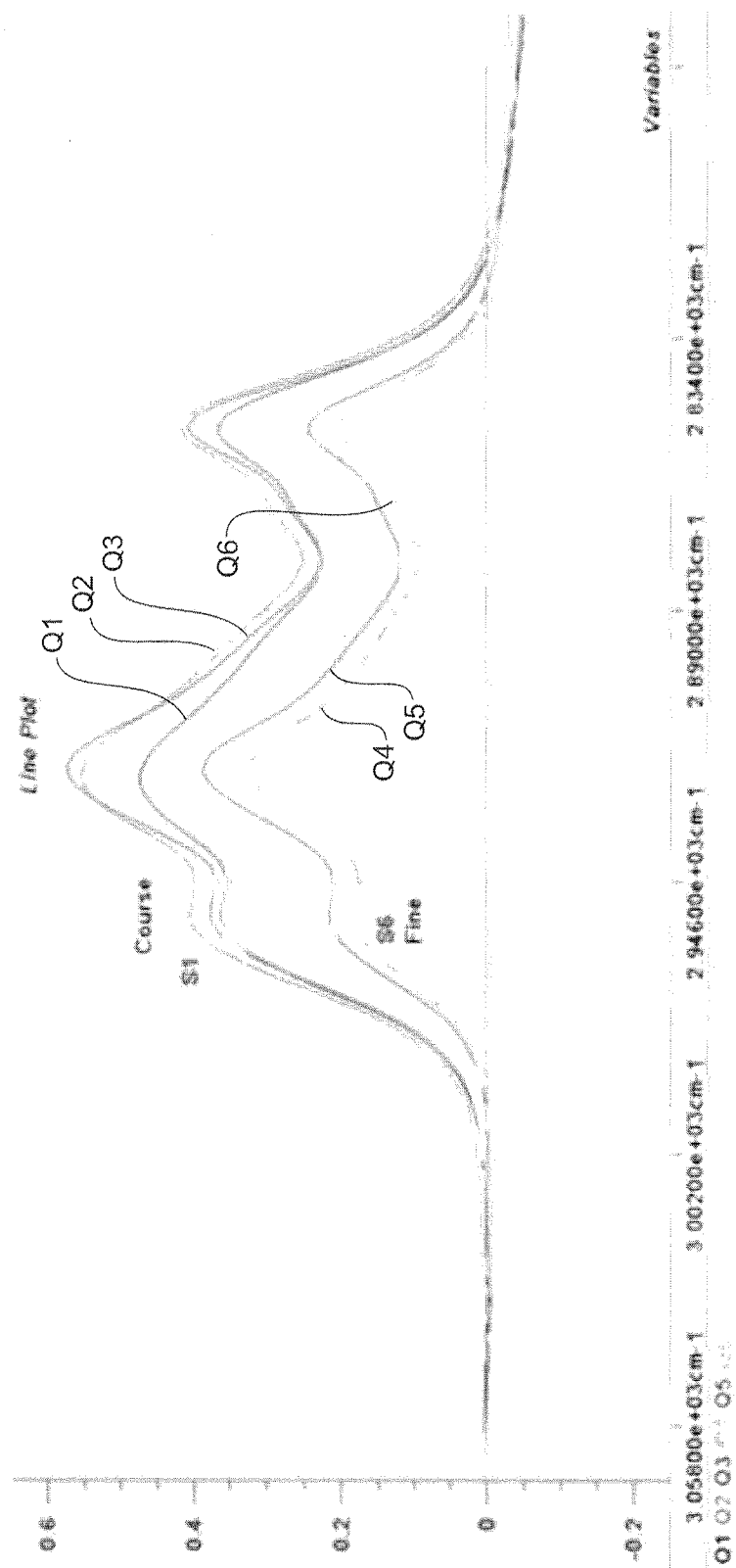

The grinding of particles was shown to result in a decrease in baseline absorbance (ie a brighter sample) and changes in the spectra in the 1360 $cm^{-1}$-2090 $cm^{-1}$ region as illustrated in FIG. 10a. Changes in absorption in the 1360 $cm^{-1}$-2090 $cm^{-1}$ spectral region were observed in quartz particles of various sizes. Further, there was a clear difference in the apparent intensity of adsorbed diesel in the finer particle sizes <500 μm. After spectral baseline correction (see FIG. 10b), a 30% reduction in the alkyl peak intensities in the fine ground quartz (S6<63 μm) was observed compared to the coarse quartz (S1 1000 μm).

Figure 11:
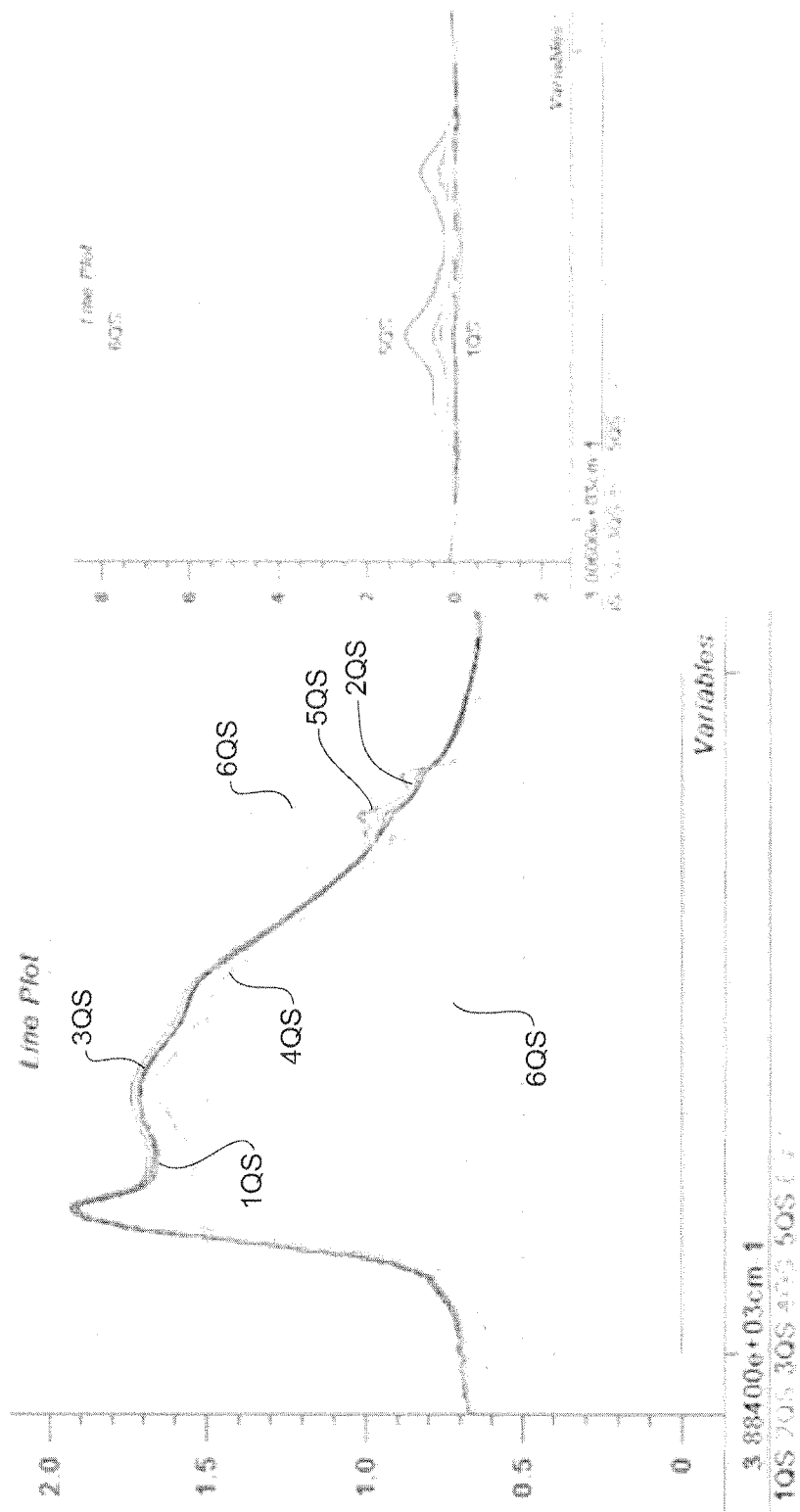
FIG. 11 shows spectra of reference sandy soil with varying proportions of smectite wherein 1% diesel is absorbed to the soil: (a) shows the spectra prior to correction and (b) shows baseline corrected spectra of 0:1 pure smectite (1QS), 1:4 sand to smectite (2QS), 1:1.5 sand to smectite (3QS), 1:0.67 sand to smectite (4QS), 1:0.25 sand to smectite (5QS) and 1:0 pure sand (6QS)
Figure 12:
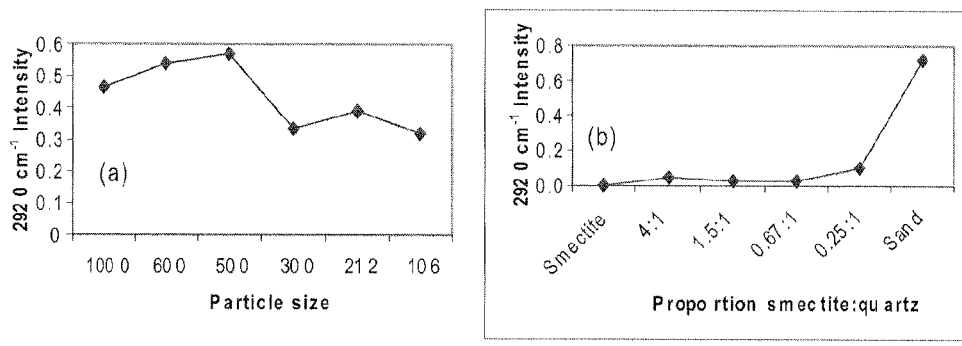
FIG. 12 shows a summary of the effect of particle size and clay proportion on 1% diesel spectral intensity: (a) shows the effect of sand particle size and (b) shows the effect of smectite (ie clay) in quartz (ie sand)

Studies were also conducted with sand mixed with varying proportions of smectite as shown in Table 4. The results are shown in FIGS. 11(a) and 11(b). Following spectra baseline correction (FIG. 11b), it was observed that the diesel alkyl signal was greater in sand than smectite. FIG. 12 shows the relationship between signal reduction due to particle size and clay content. While there is a signal reduction of about 30% due to sand particle size decrease, there is a more dramatic signal reduction, by up to a factor of 100, from mixing clay with sand and a factor of 20 for a 25% clay mixture. It appears therefore, that even small amounts of clay can reduce the apparent intensity of sorbed petroleum hydrocarbons.

PLS Modelling of Crude Oil and Diesel Adsorbed into Minerals

Figure 13:
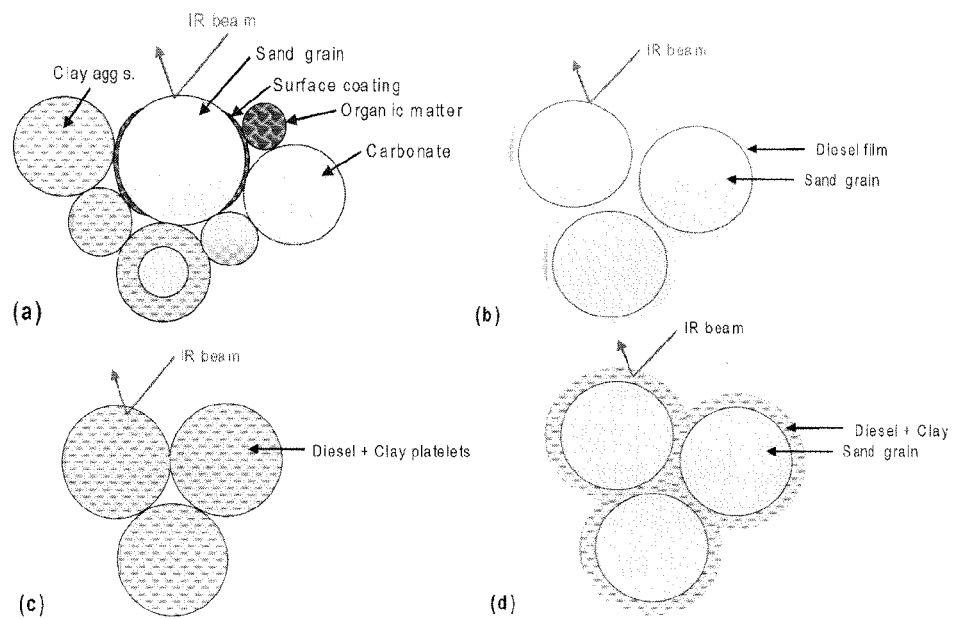
FIG. 13 provides an illustration depicting a range of soil particle variability distributions: (a) illustrates the effect of inter- and intra-particle variability by clay aggregates, sand, grains, carbonate and NOM on discrete particles and particle surfaces; (b) illustrates the effect of a diesel film coating on the surface of sand particles; (c) illustrates the effect of diesel sorbed throughout clay aggregates; and (d) illustrates the effect of clay and diesel coating on the surface of sand particles.

The effect of clay on apparent IR petroleum hydrocarbon absorbance intensities may be understood by ascertaining the mechanism of petroleum hydrocarbon signature dampening by clay particles, particularly, with respect to the distribution of petroleum hydrocarbons in or on the aggregates. As the infrared beam can only penetrate the sample to a depth of about 5 µm to 20 µm, the distribution of petroleum hydrocarbons in and on the particles is critical in determining the observed infrared intensity. FIG. 13a shows that, apart from inter-particle variability, intra-particle variability can involve the coating of large sand grains by clay, NOM and even other porous minerals such as carbonate and iron oxides. Petroleum hydrocarbons cannot sorb into sand grains, instead forming surface films as shown in FIG. 13b and resulting in strong infrared signals through mirror-like transflectance from the sand surface. Clays and other porous media absorb petroleum hydrocarbons into their interiors as shown in FIG. 13c. Since the infrared beam can only sample the surface layers, most of the absorbed petroleum hydrocarbon remains undetected by the beam resutling in reduced intensity. Even if there is a relatively thin coating of porous material on sand (FIG. 13d), signal reduction will still occur if the coating is more than about 10 µm to 20 µm. Ultimately, it is suggested that the petroleum hydrocarbon signal will be dependent on the effective particle size or surface ara of the sample. The reults shown in FIG. 9 and FIG. 12 suggest that the behaviour of crude oil sorbed onto said is an exception, with similar crude oil intensities being observed for all more porous minerals.

PLS regression models for each of the minerals reacted with crude oil and diesel according to Table 4 and Table 5, were tested to determine prediction accuracy, and detection limits, of each of the alkyl characteristic peaks. Both FT-MIR and FT-NIR were used to assess the effectiveness of the different spectral regions. In a further test of the PLS IR method, a regression was carried out using the NIRS6500 spectral data.

Table 6 summarises the results of the PLS cross-validation regression for FT-MIR, FT-NIR and NIRS6500-NIR using crude oil sorbed onto the various minerals. The data range (%) used for PLS is shown, with a 1% TPH equivalent to 10,000 mg/kg, number of samples (N), coefficient of determination ($R^2$), standard error of cross-validation (SECV), Spect1 and Spect2 are the spectral data ranges ($cm^{-1}$ for FTIR and nanometres for the NIRS6500) and spectrum type for the FTIR (MIR or NIR) and NIRS6500 for a dispersive FOSS NIR6500 spectrometer. Table 6 also shows the comparison using MIR and NIR spetral regions using the FTIR and the FOSS NIRS6500-NIR. Concentration units are expressed as mg/kg in terms of volume/weight units. In general, the prediction errors in terms of SECV and coefficient of determination ($R^2$) were within acceptable limits for the 0-10,000 mg/kg concentration range of crude oil. For this test, the FT-MIR slightly outperformed the FT-NIR. The cross-validation $R^2$ values for the FT-MIR were generally >0.96 (except for illite where the $R^2$ was only 0.79) and SECV values <7,000 mg/kg for the 0-100,000 mg/kg range of crude oil concentration. Regression analysis using the FT-NIR spectral region for illite and kaolinite in the 0-10,000 mg/kg range with crude were unsuccessful. Cross-validation predictions using the NIRS6500 spectrometer slightly outperformed the FT-MIR and FT-NIR, with $R^2$ values close to 0.99 and SECV close to 3000 mg/kg, except for smectite with crude where the SECV was about 7600 mg/kg.

We found the FTIR more promising than dispersive NIR (e.g. FOSS NIRS6500), as no commercial portable NIR compares at present with the performance of the benchtop dispersive NTR spectrometer. The use of the FTIR also makes it possible to take account of soil variability if needed, due to the in the NIR spectral region.

TABLE 4

Concentration of diesel in reference minerals comprising sand, smectite, kaolinite, illite and carbonate

| Sample/ spectra name | Tube # | Tube name | Sample treatment (diesel or crude) | matrix | Stock (mL) | Hexane (mL) | Conc of stock soln (mL TPH/mL total) | Conc TPH in sample (V/W %) | sample wt (g) | PPM |
|---|---|---|---|---|---|---|---|---|---|---|
| 1d sand | 1 | 1DS | d | sand | 0.00 | 10.00 | 0.10 | 0.00 | 10.076 | 0 |
| 2d sand | 2 | 2DS | d | sand | 5.000 | 5.000 | 0.000125 | 0.006 | 10.015 | 62 |
| 3d sand | 3 | 3DS | d | sand | 5.000 | 5.000 | 0.000250 | 0.012 | 10.042 | 124 |
| 4d sand | 4 | 4DS | d | sand | 0.05 | 9.95 | 0.10 | 0.05 | 10.009 | 499 |
| 5d sand | 5 | 5DS | d | sand | 0.10 | 9.90 | 0.10 | 0.10 | 10.034 | 996 |
| 6d sand | 6 | 6DS | d | sand | 0.25 | 9.75 | 0.10 | 0.25 | 10.046 | 2482 |
| 7d sand | 7 | 7DS | d | sand | 0.50 | 9.50 | 0.10 | 0.50 | 10.033 | 4959 |
| 8d sand | 8 | 8DS | d | sand | 1.00 | 9.00 | 0.10 | 0.99 | 10.002 | 9899 |
| 9d sand | 9 | 9DS | d | sand | 2.00 | 8.00 | 0.10 | 1.95 | 10.039 | 19533 |
| 10d sand | 10 | 10DS | d | sand | 2.50 | 7.50 | 0.10 | 2.44 | 9.996 | 24400 |
| 11d sand | 11 | 11DS | d | sand | 5.00 | 5.00 | 0.10 | 4.76 | 10.005 | 47596 |
| 12d sand | 12 | 12DS | d | sand | 7.50 | 2.50 | 0.10 | 6.97 | 10.014 | 69677 |
| 13d sand | 13 | 13DS | d | sand | 10.00 | 0.00 | 0.10 | 9.09 | 10.005 | 90868 |
| 1d smec | 1 | 1DSm | d | smec | 0.00 | 10.00 | 0.025 | 0.000 | 2.485 | 0 |
| 2d smec | 2 | 2DSm | d | smec | 1.00 | 9.00 | 0.000125 | 0.005 | 2.502 | 50 |
| 3d smec | 3 | 3DSm | d | smec | 1.00 | 9.00 | 0.000250 | 0.010 | 2.495 | 100 |
| 4d smec | 4 | 4DSm | d | smec | 0.05 | 9.95 | 0.025 | 0.05 | 2.506 | 499 |
| 5d smec | 5 | 5DSm | d | smec | 0.10 | 9.90 | 0.025 | 0.10 | 2.508 | 996 |
| 6d smec | 6 | 6DSm | d | smec | 0.25 | 9.75 | 0.025 | 0.25 | 2.5 | 2494 |
| 7d smec | 7 | 7DSm | d | smec | 0.50 | 9.50 | 0.025 | 0.50 | 2.503 | 4969 |
| 8d smec | 8 | 8DSm | d | smec | 1.00 | 9.00 | 0.025 | 0.99 | 2.502 | 9893 |
| 9d smec | 9 | 9DSm | d | smec | 2.00 | 8.00 | 0.025 | 1.96 | 2.505 | 19569 |

TABLE 4-continued

Concentration of diesel in reference minerals comprising sand, smectite, kaolinite, illite and carbonate

| | | | | | | | | | | |
|---|---|---|---|---|---|---|---|---|---|---|
| 10d smec | 10 | 10DSm | d | smec | 2.50 | 7.50 | 0.025 | 2.43 | 2.505 | 24343 |
| 11d smec | 11 | 11DSm | d | smec | 5.00 | 5.00 | 0.025 | 4.80 | 2.481 | 47966 |
| 12d smec | 12 | 12DSm | d | smec | 7.50 | 2.50 | 0.025 | 6.96 | 2.508 | 69560 |
| 13d smec | 13 | 13DSm | d | smec | 10.00 | 0.00 | 0.025 | 9.07 | 2.507 | 90678 |
| 1d kaol | 1 | 1CKa | d | kaol | 0.00 | 10.00 | 0.025 | | | |
| 2d kaol | 2 | 2CKa | d | kaol | 1.00 | 9.00 | 0.000125 | | | |
| 3d kaol | 3 | 3CKa | d | kaol | 1.00 | 9.00 | 0.00025 | | | |
| 4d kaol | 4 | 4CKa | d | kaol | 0.05 | 9.95 | 0.025 | | | |
| 5d kaol | 5 | 5CKa | d | kaol | 0.10 | 9.90 | 0.025 | | | |
| 6d kaol | 6 | 6CKa | d | kaol | 0.25 | 9.75 | 0.025 | | | |
| 7d kaol | 7 | 7CKa | d | kaol | 0.50 | 9.50 | 0.025 | | | |
| 8d kaol | 8 | 8CKa | d | kaol | 1.00 | 9.00 | 0.025 | | | |
| 1d illi | 1 | 1Cil | d | illi | 0.00 | 10.000 | 0.025 | | | |
| 2d illi | 2 | 2Cil | d | illi | 1.000 | 9.000 | 0.000125 | | | |
| 3d illi | 3 | 3Cil | d | illi | 1.000 | 9.00 | 0.00025 | | | |
| 4d illi | 4 | 4Cil | d | illi | 0.05 | 9.95 | 0.025 | | | |
| 5d illi | 5 | 5Cil | d | illi | 0.10 | 9.90 | 0.025 | | | |
| 6d illi | 6 | 6Cil | d | illi | 0.25 | 9.75 | 0.025 | | | |
| 7d illi | 7 | 7Cil | d | illi | 0.50 | 9.50 | 0.025 | | | |
| 8d illi | 8 | 8Cil | d | illi | 1.00 | 9.00 | 0.025 | | | |
| 1d CO3 | 1 | 1D-CO3 | d | CO3 | 0.00 | 10.00 | 0.025 | 0.000 | 2.503 | 0 |
| 2d CO3 | 2 | 2D-CO3 | d | CO3 | 1.00 | 9.00 | 0.000050 | 0.002 | 2.498 | 20 |
| 3d CO3 | 3 | 3D-CO3 | d | CO3 | 1.00 | 9.00 | 0.000100 | 0.004 | 2.512 | 40 |
| 4d CO3 | 4 | 4D-CO3 | d | CO3 | 0.05 | 9.95 | 0.025 | 0.05 | 2.494 | 501 |
| 5d CO3 | 5 | 5D-CO3 | d | CO3 | 0.10 | 9.90 | 0.025 | 0.10 | 2.501 | 999 |
| 6d CO3 | 6 | 6D-CO3 | d | CO3 | 0.25 | 9.75 | 0.025 | 0.25 | 2.498 | 2496 |
| 7d CO3 | 7 | 7D-CO3 | d | CO3 | 0.50 | 9.50 | 0.025 | 0.50 | 2.497 | 4981 |
| 8d CO3 | 8 | 8D-CO3 | d | CO3 | 1.00 | 9.00 | 0.025 | 0.99 | 2.511 | 9858 |
| 9d CO3 | 9 | 9D-CO3 | d | CO3 | 2.00 | 8.00 | 0.025 | 1.96 | 2.5 | 19608 |
| 10d CO3 | 10 | 10D-CO3 | d | CO3 | 2.50 | 7.50 | 0.025 | 2.44 | 2.5 | 24390 |
| 11d CO3 | 11 | 11D-CO3 | d | CO3 | 5.00 | 5.00 | 0.025 | 4.76 | 2.501 | 47601 |
| 12d CO3 | 12 | 12D-CO3 | d | CO3 | 7.50 | 2.50 | 0.025 | 6.97 | 2.504 | 69664 |
| 13d CO3 | 13 | 13D-CO3 | d | CO3 | 10.00 | 0.00 | 0.025 | 9.10 | 2.497 | 91008 |

| | |
|---|---|
| Kaolinite | Ballclay |
| Illite | Tumut |
| Carbonate | Ca-Carbonate from Univar |
| Soil Cungena from Eyre Pen | Eyre Peninsula |
| Soil ACU1 from CSIRO ACU | CSIRO ACU reference soil |
| Crude density = | 0.87 |
| PPM conversion | 1 mg/kg or 1 mg/L = 1 ppm |

TABLE 5

Concentration of crude oil in reference minerals comprising sand, smectite, kaolinite, illite and carbonate

| Sample/spectra name | Tube # | Tube name | Sample treatment (diesel or crude) | matrix | Stock (mL) | Hexane (mL) | Conc of stock soln (mL TPH/mL total) | Conc TPH in sample (V/W %) | Sample wt (g) | PPM |
|---|---|---|---|---|---|---|---|---|---|---|
| 1c sand | 1 | 1CS | c | sand | 0.00 | 10.000 | 0.10 | 0.00 | 10.029 | 0 |
| 2c sand | 2 | 2CS | c | sand | 1.00 | 9.000 | 0.000125 | 0.001 | 10.026 | 12 |
| 3c sand | 3 | 3CS | c | sand | 1.00 | 9.000 | 0.000250 | 0.002 | 10.007 | 25 |
| 4c sand | 4 | 4CS | c | sand | 0.05 | 9.950 | 0.10 | 0.05 | 10.015 | 499 |
| 5c sand | 5 | 5CS | c | sand | 0.10 | 9.90 | 0.10 | 0.10 | 10.004 | 999 |
| 6c sand | 6 | 6CS | c | sand | 0.25 | 9.75 | 0.10 | 0.25 | 10 | 2494 |
| 7c sand | 7 | 7CS | c | sand | 0.50 | 9.50 | 0.10 | 0.50 | 9.996 | 4977 |
| 8c sand | 8 | 8CS | c | sand | 1.00 | 9.00 | 0.10 | 0.99 | 10.007 | 9894 |
| 9c sand | 9 | 9CS | c | sand | 2.00 | 8.00 | 0.10 | 1.96 | 9.998 | 19612 |
| 10c sand | 10 | 10CS | c | sand | 2.50 | 7.50 | 0.10 | 2.43 | 10.048 | 24277 |
| 11c sand | 11 | 11CS | c | sand | 5.00 | 5.00 | 0.10 | 4.76 | 10.013 | 47560 |
| 12c sand | 12 | 12CS | c | sand | 7.50 | 2.50 | 0.10 | 6.98 | 9.999 | 69774 |
| 13c sand | 13 | 13CS | c | sand | 10.00 | 0.00 | 0.10 | 9.09 | 10.005 | 90868 |
| 1c smec | 1 | 1CSm | c | smec | 0.00 | 10.000 | 0.025 | 0.00 | 2.508 | 0 |
| 2c smec | 2 | 2CSm | c | smec | 1.00 | 9.000 | 0.000125 | 0.005 | 2.495 | 50 |
| 3c smec | 3 | 3CSm | c | smec | 1.00 | 9.000 | 0.000250 | 0.010 | 2.49 | 100 |
| 4c smec | 4 | 4CSm | c | smec | 0.05 | 9.95 | 0.025 | 0.05 | 2.5 | 500 |
| 5c smec | 5 | 5CSm | c | smec | 0.10 | 9.90 | 0.025 | 0.10 | 2.502 | 998 |
| 6c smec | 6 | 6CSm | c | smec | 0.25 | 9.75 | 0.025 | 0.25 | 2.498 | 2496 |
| 7c smec | 7 | 7CSm | c | smec | 0.50 | 9.50 | 0.025 | 0.50 | 2.501 | 4973 |
| 8c smec | 8 | 8CSm | c | smec | 1.00 | 9.00 | 0.025 | 0.99 | 2.494 | 9925 |
| 9c smec | 9 | 9CSm | c | smec | 2.00 | 8.00 | 0.025 | 1.96 | 2.497 | 19631 |
| 10c smec | 10 | 10CSm | c | smec | 2.50 | 7.50 | 0.025 | 2.43 | 2.505 | 24343 |
| 11c smec | 11 | 11CSm | c | smec | 5.00 | 5.00 | 0.025 | 4.77 | 2.493 | 47746 |
| 12c smec | 12 | 12CSm | c | smec | 7.50 | 2.50 | 0.025 | 7.00 | 2.49 | 70028 |

TABLE 5-continued

Concentration of crude oil in reference minerals comprising sand, smectite, kaolinite, illite and carbonate

| 13c smec | 13 | 13CSm | c | smec | 10.00 | 0.00 | 0.025 | 9.07 | 2.505 | 90744 |
|---|---|---|---|---|---|---|---|---|---|---|
| 1c kaol | 1 | 1CKa | c | kaol | 0.00 | 10.00 | 0.025 | 0.00000 | 2.493 | 0 |
| 2c kaol | 2 | 2CKa | c | kaol | 1.000 | 9.000 | 0.000125 | 0.00500 | 2.498 | 50 |
| 3c kaol | 3 | 3CKa | c | kaol | 1.000 | 9.000 | 0.00025 | 0.01002 | 2.494 | 100 |
| 4c kaol | 4 | 4CKa | c | kaol | 0.05 | 9.95 | 0.025 | 0.04984 | 2.507 | 498 |
| 5c kaol | 5 | 5CKa | c | kaol | 0.10 | 9.90 | 0.025 | 0.10046 | 2.486 | 1005 |
| 6c kaol | 6 | 6CKa | c | kaol | 0.25 | 9.75 | 0.025 | 0.24948 | 2.499 | 2495 |
| 7c kaol | 7 | 7CKa | c | kaol | 0.50 | 9.50 | 0.025 | 0.49712 | 2.502 | 4971 |
| 8c kaol | 8 | 8CKa | c | kaol | 1.00 | 9.00 | 0.025 | 0.98658 | 2.509 | 9866 |
| 1c illi | 1 | 1Cil | c | illi | 0.00 | 10.000 | 0.025 | 0.00000 | 2.493 | 0 |
| 2c illi | 2 | 2Cil | c | illi | 1.000 | 9.000 | 0.000125 | 0.00501 | 2.497 | 50 |
| 3c illi | 3 | 3Cil | c | illi | 1.000 | 9.00 | 0.000250 | 0.01002 | 2.494 | 100 |
| 4c illi | 4 | 4Cil | c | illi | 0.05 | 9.95 | 0.025 | 0.04990 | 2.504 | 499 |
| 5c illi | 5 | 5Cil | c | illi | 0.10 | 9.90 | 0.025 | 0.09970 | 2.505 | 997 |
| 6c illi | 6 | 6Cil | c | illi | 0.25 | 9.75 | 0.025 | 0.24958 | 2.498 | 2496 |
| 7c illi | 7 | 7Cil | c | illi | 0.50 | 9.50 | 0.025 | 0.49731 | 2.501 | 4973 |
| 8c illi | 8 | 8Cil | c | illi | 1.00 | 9.00 | 0.025 | 0.98697 | 2.508 | 9870 |
| 1c CO3 | 1 | 1C-CO3 | c | CO3 | 0.00 | 10.000 | 0.025 | 0.00 | 2.496 | 0 |
| 2c CO3 | 2 | 2C-CO3 | c | CO3 | 0.50 | 9.500 | 0.000250 | 0.005 | 2.501 | 50 |
| 3c CO3 | 3 | 3C-CO3 | c | CO3 | 1.00 | 9.000 | 0.000250 | 0.010 | 2.505 | 100 |
| 4c CO3 | 4 | 4C-CO3 | c | CO3 | 0.05 | 9.95 | 0.025 | 0.05 | 2.502 | 499 |
| 5c CO3 | 5 | 5C-CO3 | c | CO3 | 0.10 | 9.90 | 0.025 | 0.10 | 2.502 | 998 |
| 6c CO3 | 6 | 6C-CO3 | c | CO3 | 0.25 | 9.75 | 0.025 | 0.25 | 2.502 | 2492 |
| 7c CO3 | 7 | 7C-CO3 | c | CO3 | 0.50 | 9.50 | 0.025 | 0.50 | 2.505 | 4965 |
| 8c CO3 | 8 | 8C-CO3 | c | CO3 | 1.00 | 9.00 | 0.025 | 0.99 | 2.5 | 9901 |
| 9c CO3 | 9 | 9C-CO3 | c | CO3 | 2.00 | 8.00 | 0.025 | 1.96 | 2.5 | 19608 |
| 10c CO3 | 10 | 10C-CO3 | c | CO3 | 2.50 | 7.50 | 0.025 | 2.44 | 2.501 | 24381 |
| 11c CO3 | 11 | 11C-CO3 | c | CO3 | 5.00 | 5.00 | 0.025 | 4.75 | 2.504 | 47547 |
| 12c CO3 | 12 | 12C-CO3 | c | CO3 | 7.50 | 2.50 | 0.025 | 6.99 | 2.495 | 69897 |
| 13c CO3 | 13 | 13C-CO3 | c | CO3 | 10.00 | 0.00 | 0.025 | 9.08 | 2.503 | 90810 |

Soil Cungena from Eyre Pen    Eyre Peninsula
Soil ACU1 from CSIRO ACU    CSIRO ACU reference soil
Crude density =    0.87
PPM conversion    1 mg/kg or 1 kg/L = 1 ppm
limit for sensitive sites    1000 mg/kg (Netherlands 5000 mg/kg dry weight)

TABLE 6

Summary of PLS cross-validation regression statistics for FT-MIR, FT-NIR and NIRS6500 spectra of crude oil sorbed onto the reference minerals

| Mineral | TPH | Factors | $R^2$ | SECV | n | Data range | Spect range1 | Spect range2 | Spectrum type |
|---|---|---|---|---|---|---|---|---|---|
| Sand | crude | 2 | 0.98 | 0.39 | 10 | 0-7 | 3212-2606 | 1800-1150 | FT-MIR |
| Sand | crude | 1 | 0.78 | 0.21 | 6 | 0-1 | 3212-2606 | 1800-1150 | FT-MIR |
| Sand | diesel | 2 | 0.90 | 0.83 | 10 | 0-7 | 3110-2544 | 2168-1910 | FT-MIR |
| Sand | diesel | 1 | 0.91 | 0.32 | 8 | 0-2.5 | 3110-2544 | 2168-1910 | FT-MIR |
| Kaolinite | crude | 1 | 0.97 | 0.07 | 8 | 0-1 | 3108-2770 | | FT-MIR |
| Illite | crude | 1 | 0.79 | 0.19 | 7 | 0-1 | 3108-2770 | | FT-MIR |
| Smectite | crude | 2 | 0.96 | 0.71 | 11 | 0-10 | 4000-550 | | FT-MIR |
| Smectite | diesel | 2 | 0.99 | 0.24 | 13 | 0-10 | 4000-550 | | FT-MIR |
| Carbonate | crude | 1 | 0.97 | 0.55 | 13 | 0-10 | 4000-450 | | FT-MIR |
| Carbonate | diesel | 1 | 0.98 | 0.42 | 13 | 0-10 | 4000-450 | | FT-MIR |
| Sand | crude | 1 | 0.89 | 0.81 | 12 | 0-7 | 4038-4386 | 5596-5948 | FT-NIR |
| Sand | diesel | 1 | 0.84 | 1.38 | 11 | 0-10 | 4000-6000 | | FT-NIR |
| Smectite | crude | 1 | 0.95 | 0.72 | 13 | 0-10 | 4402-4234 | 5884-5646 | FT-NIR |
| Smectite | diesel | 2 | 0.97 | 0.63 | 11 | 0-10 | 4000-6034 | | FT-NIR |
| Carbonate | crude | 1 | 0.98 | 0.48 | 13 | 0-10 | 7800-4000 | | FT-NIR |
| Carbonate | diesel | 1 | 0.98 | 0.45 | 13 | 0-10 | 7800-4000 | | FT-NIR |
| Sand | crude | 1 | 0.99 | 0.31 | 11 | 0-10 | 400-2499 | | NIRS6500 |
| Sand | diesel | 1 | 0.99 | 0.30 | 13 | 0-10 | 400-2500 | | NIRS6500 |
| Smectite | crude | 1 | 0.95 | 0.76 | 11 | 0-10 | 1368-1410 | 1676-2500 | NIRS6500 |
| Smectite | diesel | 1 | 0.99 | 0.26 | 13 | 0-10 | 400-2501 | | NIRS6500 |

Example 2

Determination of TPH in Field Samples

Soil samples were taken from two geographically separated contaminated sites. The site one samples consisted of 93 samples from 32 soil pits, with TPH concentrations ranging from 0-33,000 mg/kg. The site two samples consisted of 45 samples with concentrations ranging from 0-26,000 mg/kg.

Neat samples were scanned using an FTIR spectrometer, spectral range 7800-450 cm$^{-1}$ at a resolution of 8 cm$^{-1}$. The spectra were then referenced against laboratory derived reference TPH data and then assessed for robustness.

The spetra measurements suggested that infrared signals at or near 2830 cm$^{-1}$ and 2870 cm$^{-1}$, may be useful in addition to those signal frequencies already discussed, and may be used to differentiate between natural and petroleum derived hydrocarbons. The frequencies at or near 2830 cm$^{-1}$ and 2870 cm$^{-1}$ represent the outer "wings" of a main —CH$_2$— peak centred at or near 2850 cm$^{-1}$.

For site one, using the full concentration range and only the 2730 cm$^{-1}$ peak, a linear model was formed with an R$^2$=0.90 and SEP=1434 mg/kg (SEP=standard error of prediction).

A skewed TPH concentration distribution was apparent in this set of samples, with most samples bunched below 2500 mg/kg, only 5 samples >2500 mg/kg, and at least 3 samples with high errors at low concentrations.

To investigate if the prediction potential of the PLS models could be improved, a PLS cross validation regression was carried out at the lower concentration range of 0-1500 mg/kg rather than the full concentration range. Additionally, using intensities at 2830 cm$^{-1}$ and 2870 cm$^{-1}$ for the modelling, rather than the 2730 cm$^{-1}$ peak, a similar if not slightly improved model was formed at this lower concentration range, compared to using only the 2730 cm$^{-1}$ peak over this range, although the 2730 cm$^{-1}$ peak modelled the 3 high-error samples mentioned above better.

The above models were tested by predicting the unknown samples from site 2, with the (0-1500 mg/kg, 2730 cm$^{-1}$) model performing best. Prediction of site 2 samples from the 2730 cm$^{-1}$ full range model resulted in an R$^2$=0.93. Use of the restricted range model using intensities near 2830/2870 cm$^{-1}$ resulted in an R$^2$=0.92 if a quadratic function (2$^{nd}$ order polynomial) was applied to the laboratory vs predicted data.

At a third geographically separate site from the two mentioned above, a further 15 samples were collected in duplicate, with one analysed on the laboratory using traditional methods as described above for TPH and the other taken for spectral analysis. Spectra and laboratory data were combinated in a PLS model and investigated as described previously. During analysis the previously defined peaks specific to TPH were assessed along with others described below. The concentration range for these new samples was from 0-6300 mg/kg TPH.

For these samples, a further peak of possible interested was identified at 4330 cm$^{-1}$ and assigned to CH$_2$ combination/ overtone vibrations. Use of this peak alone resulted in a model with good performance (R$^2$=0.83, SECV=782), similar to results using the combination and overtone peak at 2730 cm$^{-1}$ alone (R$^2$=0.82, SECV=882). A combination of these two peaks resulted in a slight improvement (R$^2$=0.84, SECV=801).

CONCLUSIONS

The use of infrared reflectance spectroscopy with PLS chemometrics to predict TPH in materials with widely variable mineralogy should preferably overcome difficulties associated with an overlap of TPH peaks by carbonate peaks, an overlap of TPH peaks by natural organic matter peaks, and the variable sorption into different minerals due to particle size, as this may lead to variable signal strength and detection limits for different types of environmental matrices. The results obtained in this example show that the PLS method may be used to model the relationship between TPH signal strength and concentration by taking into account sample composition or matrix type. The inclusion of spectral signatures from quartz in the PLS X-variable data, or otherwise providing a way for the PLS model to differentiate between sorption onto quartz and sorption onto other environmental materials, may further improve TPH prediction. Moreover, the disproportionate spectra reflectance from large sand grains may be reduced by eliminating particle size effects. It was observed that even a small amount of a clay material can dramatically reduce the TPH spectral intensity, and that this effect plateaus at about 50% clay. The plateau effect may be exploited by mixing all samples with a known weight of a diluent such as an alkali halide (eg KBr) or even fine clay. This would have the effect of covering the sand grains with a shielding agent and also sorbing some of the surface TPH film into this fine material.

The examples also show that infrared signals near 2730 cm$^{-1}$, 2830 cm$^{-1}$, 2870 cm$^{-1}$, 1380 (~1360-1380) cm$^{-1}$, 2950 cm$^{-1}$, 4164 cm$^{-1}$ and 4330 cm$^{-1}$ may be used to differentiate between natural and petroleum derived hydrocarbons.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

REFERENCES

Adams, M J, Awaja, F, Bhargava, S, Grocott, S & Romeo, M. Prediction of oil yield from oil shale minerals using diffuse reflectance infrared Fourier transform spectroscopy. *Fuel* 84: 1986-1991 (2005).

Geladi, P & Kowalski, B R. Partial least-squares regression: a tutorial. *Analytica Chimica Acta* 185:1-17(1986).

Gomez, R S G. Spectroscopic determination of poly-aromatic compounds in petroleum contaminated soils. *Water, Air and Soil Pollution* 158:137-151 (2004).

Janik, L J, Merry, R H & Skjemstad, J O. Can mid infrared diffuse reflectance analysis replace soil extractions? *J. Exp. Agric.* 38:681-696 (1998).

Nadim, F. A comparison of spectrophotometric and gas chromatographic measurements of heavy petroleum products in soil samples. *Water, Air and Soil Pollution* 134:97-109 (2002).

Malley, D F, Hunter, K N & Barrie Webster, G R. Analysis of diesel fuel contamination in soils by near-infrared reflectance spectrometry and solid phase microextraction-gas chromatography. *J. Soil Contam.* 8:481-489 (1999).

McCarty G W, Reeves J B, Reeves V B, et al. Mid-infrared and near-infrared diffuse reflectance spectroscopy, for soil carbon measurement. *Soil Science Society of America Journal* 66(2):640-646 (2002).

Rayment, G & Higginson, H., Australian Laboratory Handbook of Soil and Chemical Methods, Australian Soil and Land Survey Handbook, Inkata Press, (1992).

Reeves J B, McCarty G W, & Meisinger J J. Near infrared reflectance spectroscopy for the analysis of agricultural soils. *Journal of near infrared spectroscopy* 7(3):179-193 (1999).

Sadler, R & Connell, D. Analytical methods for the determination of total petroleum hydrocarbons in soil, *Proceedings of the 5th national workshop on the assessment of site contamination* pp 133-150 (2003).

Van der Marel H W & Beutelspacher H. Clay and related minerals. In "Atlas of infrared spectroscopy of clay minerals and their admixtures". (Elsevier Scientific: Amsterdam) (1976).

Zwanziger, H W & Förster, H. Near infrared spectroscopy of fuel contaminated sand and soil. I. preliminary results and calibration study. *Near Infrared Spectroscopy* 6:189-197 (1998).

The invention claimed is:

1. A method for the selective detection of total petroleum hydrocarbon (TPH) in an environmental sample containing natural organic matter (NOM) by diffuse reflectance spectroscopy, the method comprising the steps of:
    (i) providing TPH concentration regression models that have been obtained by performing multivariate regression analysis on data obtained by correlating the TPH concentration of one or more reference samples comprising known amounts of TPH with absorbance values of infrared (IR) signal(s) representative of TPH in the sample(s) centered on a signal at $1380 \text{ cm}^{-1}$, $2690 \text{ cm}^{-1}$, $2730 \text{ cm}^{-1}$, $2830 \text{ cm}^{-1}$, $2870 \text{ cm}^{-1}$, $4164 \text{ cm}^{-1}$, $4256 \text{ cm}^{-1}$, $4329 \text{ cm}^{-1}$ and/or $4388 \text{ cm}^{-1}$;
    (ii) subjecting the environmental sample to IR radiation, and detecting an IR signal centered on a signal at $1380 \text{ cm}^{-1}$, $2690 \text{ cm}^{-1}$, $2730 \text{ cm}^{-1}$, $2830 \text{ cm}^{-1}$, $2870 \text{ cm}^{-1}$, $4164 \text{ cm}^{-1}$, $4256 \text{ cm}^{-1}$, $4329 \text{ cm}^{-1}$ and/or $4388 \text{ cm}^{-1}$ to provide predictive TPH data;
    (iii) analyzing the predictive TPH data using the TPH concentration regression models; and
    (iv) providing an output TPH concentration of the environmental sample based on the analysis performed at step (iii), wherein said output TPH concentration is substantially independent of the presence of NOM in the environmental sample.

2. The method according to claim 1, wherein the environmental sample is crushed, ground and/or sieved prior to step (ii).

3. The method according to claim 1, wherein the environmental sample is dried prior to step (ii).

4. The method according to claim 1, wherein the environmental sample is mixed with a diluent prior to step (ii).

5. The method according to claim 4, wherein the diluent is an alkali halide or fine clay.

6. The method according to claim 1, wherein step (ii) involves diffuse reflectance infrared fourier transform spectroscopy (DRIFT).

7. The method according to claim 1 comprising detecting IR signals at two or more wavenumbers in step (ii).

8. The method according to claim 1, wherein the multivariate regression analysis is based on partial least squares regression.

9. The method according to claim/, wherein the environmental sample is selected from the group consisting of soil, silt, sediment, rock, mineral, and waste.

10. The method according to claim 1, wherein the environmental sample is subjected to IR using a portable diffusion reflectance infrared spectrometer.

11. The method according to claim 1, wherein the environmental sample is subjected to IR directly without any preprocessing or treatment of the sample.

12. The method according to claim 1, wherein the environmental sample is in situ when it is subjected to IR.

* * * * *